United States Patent
Oyadomari

(10) Patent No.: US 9,085,791 B2
(45) Date of Patent: Jul. 21, 2015

(54) METHOD FOR SCREENING SUBSTANCE RELATING TO ENDOPLASMIC RETICULUM STRESS PARTICIPATING IN ONSET OF DIABETES

(75) Inventor: Seiichi Oyadomari, Tokushima (JP)

(73) Assignee: THE UNIVERSITY OF TOKUSHIMA, Tokushima-Shi (JP)

( * ) Notice: Subject to any disclaimer, the term of this patent is extended or adjusted under 35 U.S.C. 154(b) by 0 days.

(21) Appl. No.: 13/983,864

(22) PCT Filed: Feb. 6, 2012

(86) PCT No.: PCT/JP2012/052650
§ 371 (c)(1),
(2), (4) Date: Aug. 6, 2013

(87) PCT Pub. No.: WO2012/108394
PCT Pub. Date: Aug. 16, 2012

(65) Prior Publication Data
US 2013/0344530 A1    Dec. 26, 2013

(30) Foreign Application Priority Data
Feb. 7, 2011    (JP) ................................. 2011-023697

(51) Int. Cl.
*C07K 19/00*    (2006.01)
*C12Q 1/02*    (2006.01)
*G01N 33/50*    (2006.01)
*C07K 14/47*    (2006.01)

(52) U.S. Cl.
CPC .............. *C12Q 1/025* (2013.01); *C07K 14/472* (2013.01); *C12Y 104/03002* (2013.01); *G01N 33/5008* (2013.01); *G01N 33/5076* (2013.01); *C07K 2319/60* (2013.01); *G01N 2333/4706* (2013.01); *G01N 2500/10* (2013.01); *G01N 2800/042* (2013.01)

(58) Field of Classification Search
None
See application file for complete search history.

(56) References Cited

U.S. PATENT DOCUMENTS

| | | | |
|---|---|---|---|
| 7,585,636 B2 * | 9/2009 | Waldo et al. | 435/7.1 |
| 2006/0257942 A1 * | 11/2006 | Waldo et al. | 435/7.2 |
| 2007/0196354 A1 | 8/2007 | Doi | |
| 2009/0281040 A1 * | 11/2009 | Urano et al. | 514/12 |

FOREIGN PATENT DOCUMENTS

| | | | |
|---|---|---|---|
| JP | 2001-66302 A1 | 3/2001 | |
| JP | 2004-81143 A1 | 3/2004 | |
| JP | 2005-65692 A1 | 3/2005 | |
| JP | 2005-204516 A1 | 8/2005 | |
| JP | 2008-131899 A1 | 6/2008 | |
| WO | WO 2005/030255 A1 | 4/2005 | |
| WO | WO 2006/062877 A2 | 6/2006 | |

OTHER PUBLICATIONS

Gkogkas et al. VAPB Interacts With and Modulates the Activity of ATF6; Human Molecular Genetics, vol. 17, No. 11 (2008) pp. 1517-1526.*
Nadanaka et al. Activation of mammalian unfoleded protein response is compatible with the quality control system operating in the endoplasmic reticulum. Molecular Biology of the Cell, vol. 15, pp. 2537-2548, Jun. 2004.*
Yaglom et al. p34Cdc28-mediated control of Cln3 cyclin degradation. Molecular and Cellular Biology, vol. 15, No. 2, pp. 731-741, Feb. 1995.*
Remy et al. PKB/Akt modulates TGF-beta signalling through a direct interaction with Smad3. Nature Cell Biology, vol. 6, No. 4, pp. 358-365, Apr. 2004.*
K. Cawley, et al.; "Assays for Detecting the Unfolded Protein Response;" Methods in Enzymology; vol. 490; 2011; pp. 31-51 and end sheet (22 Sheets), available online Jan. 13, 1011.
Y. Shyu, et al.; "Fluorescence complementation: an emerging tool for biological research;" Trends in Biotechnology; vol. 26; No. 11; pp. 622-630 (9 Sheets), 2008.
S. Bale, et al.; "A GFP Complementation System for Monitoring and Directing Nanomaterial Mediated Protein Delivery to Human Cellular Organelles;" Biotechnology and Bioengineering; vol. 107; No. 6; 2010; pp. 1040-1047; 8 Sheets).
S. Tsutsumi, et al.; "Endoplasmic reticulum stress response is involved in nonsteroidal anti-inflammatory drug-induced apoptosis;" Cell Death and Differentiation; vol. 11; No. 9; 2004; pp. 1009-1016 (8 Sheets).
D. Ron, et al.; "Signal integration in the endoplasmic reticulum unfolded protein response;" Nature Reviews Molecular Cell Biology; vol. 8; No. 7; Jul. 2007; pp. 519-529 (11 Sheets).
K. Yamamoto, et al.; "Induction of Liver Steatosis and Lipid Droplet Formation in ATF6α-Knockout Mice Burdened with Pharmacological Endoplasmic Reticulum Stress;" Molecular Biology of the Cell; vol. 21; Sep. 1, 2010; pp. 2975-2986 and cover sheet (13 Sheets).
International Search Report for International Application No. PCT/JP2012/052650 dated Apr. 17, 2012.
Kitsera, N., et al., "Destabilized green fluorescent protein detects rapid removal of transcription blocks after genotoxic exposure." BioTechniques, vol. 43, No. 2, 2007.
Corish, P., et al., "Attenuation of green fluorescent protein half-life in mammalian cells," Protein Engineering, vol. 12, No. 12, pp. 1035-1040, 1999.

* cited by examiner

Primary Examiner — Jennifer Dunston
(74) Attorney, Agent, or Firm — Kratz, Quintos & Hanson, LLP

(57) ABSTRACT

A system for evaluating activation of the pathway mediated by ATF6. More specifically, a method for screening an endoplasmic reticulum stressor, as well as a method for screening a substance for suppressing an endoplasmic reticulum stress induced by the activation of the pathway mediated by ATF6, and a method for screening an antidiabetic drug candidate. A method for real-time evaluation of activation of the pathway mediated by ATF6 in viable cells. The method uses a polynucleotide encoding a nonfluorescent peptide domain derived from a fluorescent protein and an ATF6 protein domain.

6 Claims, 14 Drawing Sheets

FIG. 4

EGFPS-ATF6d (Nhe1-Not1) (SEQ ID NO: 17)

CTAgccacc
ATGCGTGACCACATGGTCCTTCATGAGTACGTAAATGCTGCTGGGATTACA — Portion 1 (SEQ ID NO: 18)

ggaggaggatccggaggtggcagc — Portion 2 (SEQ ID NO: 19)

GACTACAAAGACCATGACGGTGATTATAAAGATCATGACATCGACTACAAGGATGA
CGATGACAAG — Portion 3 (SEQ ID NO: 20)

gatccaaaaaagaagagaaaggtagatccaaaaaagaagagaaaggtagatccaaaaaagaagagaaaggta — Portion 4 (SEQ ID NO: 21)

CTAGCGCTACCGGACTCAGATCTCGAG
agccatggcttcccgccggcggtggcggcgcaggatgatggcacgctgcccatgtcttgtgcccaggagagcgggatggacc
gtcaccctgcagcctgtgcttctgctaggatcaatgtg — Portion 5 (SEQ ID NO: 22)
GGTACC ccaaagcgaagagctgtctgtgtgatgatagtattagcatttataatgctgaactatgggcccatgagcatgctggagcaag
aatcccgaagagtgaaacctagtgtgagccctgccaatcagaggaggcatctcttggaattttcagcaaaagaagttaaag
acacatcagatggtgacaaccagaaagacagttacagctatgatcactctgtgtccaatgacaaagctttaatggtgctaag
tgaagagccattgctttatatgcctccacctccatgtcaaccctgattaacacaacagagtctctcaggttgaaccatgaactt
cgaggctgggttcatagacatgaagtggaaaggaccaaatctagaagaatgacaaatagccaacagaaagcccgcattct
ccagggtgctctggaacagggctctaattctcagctgatggctgtccagtacacagaaaccactagcatcagtaggaattctg — Portion 6 (SEQ ID NO: 23)
ggagtgagctgcaagtgtattacgcctcccctggaagttaccaaggcttctttgacgccatccgcaggaggggagatacgttt
tacgttgtctcatttcgaagggatcatctgctattaccagctaccacccacaacaagaccacaagaccaaaaatgtcaattgt
attaccagcaataaacataaatgataatgtgatcaatgggcaggactatgaagtaatgatgcagattgactgtcaggtgat
ggacaccaggatcctccacatcaaaagctcctcggttcccccttatctccgggatcatcagcggaaccaaaccagcaccttctt
tggttcccctccaacaaccacagagacgacccatgtggtcagcaccatccctgagtcgttgcagtag
GC

FIG. 5

EGFPL (Nhe1-Not1) (SEQ ID NO: 24)

ctaGCCACCATG
gatccaaaaaagaagagaaaggtagatccaaaaaagaagagaaaggtagatccaaaaaagaagagaaaggta    Portion 7
(SEQ ID NO: 25)

ATGGTGAGCAAGGGCGAGGAGCTGTTCACCGGGGTGGTGCCCATCCTGGTCGAGC
TGGACGGCGACGTAAACGGCCACAAGTTCAGCGTGagaGGCGAGGGCGAGGGCGA
TGCCACCatcGGCAAGCTGACCCTGAAGTTCATCTGCACCACCGGCAAGCTGCCCG
TGCCCTGGCCCACCCTCGTGACCACCCTGACCTACGGCGTGCAGTGCTTCAGCCG
CTACCCCGACCACATGAAGaggCACGACTTCTTCAAGTCCGCCATGCCCGAAGGCT
ACGTCCAGGAGCGCACCATCtctTTCAAGGACGACGGCAaaTACAAGACCCGCGCCgt
aGTGAAGTTCGAGGGCGACACCCTGGTGAACCGCATCGAGCTGAAGGGCactGACT    Portion 8
TCAAGGAGGACGGCAACATCCTGGGGCACAAGCTGGAGTACAACtttAACAGCCAC    (SEQ ID NO: 26)
AACGTCTATATCacgGCCGACAAGCAGAAGAACGGCATCAAGGgctAACTTCacagttCGC
CACAACgttGAGGACGGCAGCGTGCAGCTCGCCGACCACTACCAGCAGAACACCCC
CATCGGCGACGGCCCCGTGCTGCTGCCCGACAACCACTACCTGAGCACCCAGactgt
cCTGAGCAAAGACCCCAACGAGAAGtaa
agc

FIG. 9

**DNA sequence in which only the spacer is changed to
a sequence GGGS**

TACGTAAATGCTGCTGGGATTACAGGAGGTGGCAGCGACTACAAAGACCATGACG
GTGATTATAAAGATCATGACATCGACTACAAGGATGACGATGACAAGGATCCAAAA    SEQ ID NO: 27
AAGAAGAGAAAGGTAGATCCAAAAAAGAAGAGAAAGGTAGATCCAAAAAAGAAGA
GAAAGGTACTAGCGCTACCGGACTCAGATCT

**DNA sequence in which only the spacer is changed to
a sequence GGGSGGGSGGGS**

TACGTAAATGCTGCTGGGATTACAGGAGGAGGATCCGGAGGTGGCAGCGGAGGTG
GCAGCGACTACAAAGACCATGACGGTGATTATAAAGATCATGACATCGACTACAAG
GATGACGATGACAAGGATCCAAAAAAGAAGAGAAAGGTAGATCCAAAAAAGAAGA    SEQ ID NO: 28
GAAAGGTAGATCCAAAAAAGAAGAGAAAGGTACTAGCGCTACCGGACTCAGATCT

ERAI system

UMAI system

METHOD FOR SCREENING SUBSTANCE RELATING TO ENDOPLASMIC RETICULUM STRESS PARTICIPATING IN ONSET OF DIABETES

TECHNICAL FIELD

The present invention relates to a method for screening an endoplasmic reticulum stressor or endoplasmic reticulum stress inhibitor; or a method for screening an antidiabetic drug candidate.

BACKGROUND ART

A typical biological stress involved in the onset of diabetes is oxidative stress. Further, a new biological stress called endoplasmic reticulum stress has been found recently; research has gradually revealed that, similar to biological stress, endoplasmic reticulum stress is considered relevant to diabetes.

Endoplasmic reticulum stress designates an accumulation of irregular proteins in the endoplasmic reticulum. More specifically, endoplasmic reticulum stress is caused by failure of proper folding of proteins due to physical or chemical stimulation exerted on unstable incomplete proteins during the biosynthesis in the endoplasmic reticulum. In the endoplasmic reticulum, the unstable incomplete proteins during the biosynthesis are susceptible to physical or chemical stimulation, and such stimulation converts the proteins into abnormal proteins having an abnormal folding structure. Although the properly folded proteins are transported from the endoplasmic reticulum to the Golgi apparatus, the unfolded or misfolded proteins are stored inside the endoplasmic reticulum.

Cells are assumed to address endoplasmic reticulum stress using at least three methods below.
(1) a method of increasing the amount of molecular chaperones or the like in the endoplasmic reticulum, thereby protecting the proteins accumulated in the endoplasmic reticulum (UPR: unfolded protein response);
(2) a method of reducing the amount of protein entering into the endoplasmic reticulum, thereby reducing the load; and
(3) a method of degrading proteins accumulated in the endoplasmic reticulum by cytoplasm (ERAD: ER-associated protein degradation).

However, when the stress significantly outperforms these defense mechanisms, or when the defense mechanisms malfunction due to some sort of error, the stress is assumed to result in cell death. The characteristics of such cell death resulting from endoplasmic reticulum stress is morphologically the same as apoptosis, and is accompanied by expression induction or activation of molecules called CHOP, JNK, and caspase.

Recent study has revealed that such cell death derived from endoplasmic reticulum stress is deeply involved in various diseases including neurodegenerative disorders such as diabetes, Parkinson's disease, Alzheimer's disease, polyglutamine disease, prion disease, or amyotrophic lateral sclerosis (ALS); and ischemic disorders. Therefore, finding a method of overcoming cell death originating from endoplasmic reticulum stress is believed to provide a new treatment for various diseases.

Under such circumstances, research on the measurement of endoplasmic reticulum stress or the discovery of substances involved in endoplasmic reticulum stress has been conducted in various fields (for example, see Patent Documents 1 to 4). However, the relevance of certain substances to the mechanism of endoplasmic reticulum stress is still unclear.

CITATION LIST

Patent Documents

[Patent Document 1] JP2008-131899A
[Patent Document 2] JP2005-204516A
[Patent Document 3] JP2005-065692A
[Patent Document 4] JP2004-081143A

SUMMARY OF INVENTION

Technical Problem

As shown in FIG. 1, the endoplasmic reticulum stress that occurs in the endoplasmic reticulum is transmitted to cytoplasm through an endoplasmic reticulum membrane via three kinds of endoplasmic reticulum transmembrane proteins (IRE1α, PERK, and ATF6). Further, the cellular response to the endoplasmic reticulum stress depends on whether all or a part of the pathways among the pathways corresponding to the three endoplasmic reticulum transmembrane proteins is activated, and depends on the type (IRE1α, PERK, and/or ATF6) of the pathway activated. Therefore, in order to grasp the cellular response mechanism, or to establish a method for treating diabetes or neurodegenerative disorders caused by endoplasmic reticulum stress, it is very important to create a system for finding a certain substance or physiological/pathological environment that relates to activation of a certain pathway or all of the pathways mediated by the above three endoplasmic reticulum transmembrane proteins.

However, until now, among the pathways mediated by the above three endoplasmic reticulum transmembrane proteins, only a system for evaluating activations of pathways mediated by IRE1α and PERK is known, and a system for evaluating activation of the pathway mediated by ATF6 has not been established. Further, when the system for evaluating pathway activation is used for screening an endoplasmic reticulum stressor, an endoplasmic reticulum stress inhibitor, or an antidiabetic drug candidate, the system must be capable of real-time evaluation of viable cells with a high degree of sensitivity, so as to enable rapid and highly accurate screening.

An object of the present invention is to provide a system for evaluating activation of the pathway mediated by ATF6. More specifically, an object of the present invention is to provide a method for screening an endoplasmic reticulum stressor that activates the pathway mediated by ATF6, and another object of the present invention is to provide a method for screening a substance that suppresses endoplasmic reticulum stress caused by activation of the pathway mediated by ATF6; and a method for screening an antidiabetic drug candidate.

Technical Solution

As a result of extensive research, the inventors of the present invention found a method for real-time evaluation of activation of the pathway mediated by ATF6 in viable cells with a high degree of sensitivity. The method uses a nonfluorescent peptide domain derived from a fluorescent protein and a polynucleotide encoding the ATF6 protein domain.

Specifically, the present invention has the following aspects.

Item 1. A polynucleotide encoding an amino acid sequence having a nonfluorescent peptide domain 1 derived from a fluorescent protein constituted of a nonfluorescent peptide domain 1 and a nonfluorescent peptide domain 2, and an ATF6 protein domain.

Item 2. The polynucleotide according to Item 1, wherein the polynucleotide has a region encoding a nonfluorescent peptide domain 1 derived from a fluorescent protein at the 5' end, and a region encoding an ATF6 protein domain at the 3' end.

Item 3. The polynucleotide according to Item 1 or 2, wherein the polynucleotide encodes an amino acid sequence in which the nonfluorescent peptide domain 1 derived from a fluorescent protein and the ATF6 protein domain are connected via a spacer.

Item 4. A transgenic vector comprising the polynucleotide according to any one of Items 1 to 3.

Item 5. A transformant comprising a transgenic vector according to Item 4.

Item 6. The transformant according to Item 5, further comprising a nonfluorescent peptide domain 2 derived from a fluorescent protein constituted of a nonfluorescent peptide domain 1 and a nonfluorescent peptide domain 2, and a polynucleotide encoding an amino acid sequence having a nuclear localization signal peptide domain, in a state where a protein having the amino acid sequence can be expressed.

Item 7. The transformant according to Item 6, wherein the transformant is a pancreatic β-cell comprising the vector of Item 4, a nonfluorescent peptide domain 2 derived from a fluorescent protein constituted of a nonfluorescent peptide domain 1 and a nonfluorescent peptide domain 2, a polynucleotide encoding an amino acid sequence having a nuclear localization signal peptide domain, in a state where the protein having the amino acid sequence can be expressed.

Item 8-1. A method for screening an endoplasmic reticulum stressor, comprising the steps of:
(a) bringing an endoplasmic reticulum stressor candidate substance into contact with the transformant of Item 6;
(b) measuring the fluorescence intensity of the transformant in contact with the endoplasmic reticulum stressor candidate substance, and comparing the measured fluorescence intensity with the fluorescence intensity of a control transformant not in contact with the endoplasmic reticulum stressor candidate substance; and
(c) selecting the endoplasmic reticulum stressor candidate substance as an endoplasmic reticulum stressor when the fluorescence intensity of the transformant in contact with the endoplasmic reticulum stressor candidate substance is higher than the fluorescence intensity of the control transformant.

Item 8-2. A method for screening an organ-specific endoplasmic reticulum stressor, comprising the steps of:
(a') bringing an organ-specific endoplasmic reticulum stressor candidate substance into contact with the transformant of Item 6;
(b') measuring the fluorescence intensity of the transformant in contact with the organ-specific endoplasmic reticulum stressor candidate substance, and comparing the measured fluorescence intensity with the fluorescence intensity of a control transformant not in contact with the organ-specific endoplasmic reticulum stressor candidate substance; and
(c') selecting the organ-specific endoplasmic reticulum stressor candidate substance as an organ-specific endoplasmic reticulum stressor when the fluorescence intensity of the transformant in contact with the organ-specific endoplasmic reticulum stressor candidate substance is higher than the fluorescence intensity of the control transformant.

Item 9-1. The method according to Item 8-1 or 8-2, wherein the endoplasmic reticulum stressor is an endoplasmic reticulum stressor that activates ATF6 pathway, but does not activate IRE1α pathway or PERK pathway; or an endoplasmic reticulum stressor that activates ATF6 pathway, and IRE1α pathway and/or PERK pathway.

Item 9-2. The method according to Item 8-1 or 8-2, wherein the endoplasmic reticulum stressor is:
an endoplasmic reticulum stressor that activates ATF6 pathway, but does not activate IRE1α pathway or PERK pathway,
an endoplasmic reticulum stressor that activates ATF6 pathway, and IRE1α pathway and/or PERK pathway, or
an endoplasmic reticulum stressor that does not activate ATF6 pathway, but activates IRE1α pathway and/or PERK pathway.

Item 10-1. A method for screening an endoplasmic reticulum stress inhibitor, comprising the steps of:
(d) bringing an endoplasmic reticulum stressor and a test substance with the transformant of Item 6;
(e) measuring the fluorescence intensity of the transformant in contact with the endoplasmic reticulum stressor and the test substance, and comparing the measured fluorescence intensity with the fluorescence intensity of a control transformant that is not in contact with the test substance, but that is in contact with the endoplasmic reticulum stressor; and
(f) selecting the test substance as an endoplasmic reticulum stress inhibitor when the fluorescence intensity of the transformant in contact with the endoplasmic reticulum stressor and the test substance is higher than the fluorescence intensity of the control transformant.

Item 10-2. A method for screening a substance for organ-specifically suppressing endoplasmic reticulum stress, comprising the steps of:
(d') bringing an endoplasmic reticulum stressor and a test substance with the transformant of Item 6;
(e') measuring the fluorescence intensity of the transformant in contact with the endoplasmic reticulum stressor and the test substance, and comparing the measured fluorescence intensity with the fluorescence intensity of a control transformant that is not in contact with the test substance but that is in contact with the endoplasmic reticulum stressor; and
(f') selecting the test substance as a substance for organ-specifically suppressing endoplasmic reticulum stress when the fluorescence intensity of the transformant in contact with the endoplasmic reticulum stressor and the test substance is higher than the fluorescence intensity of the control transformant.

Item 11. A method for screening an antidiabetic drug candidate, comprising the steps of:
(g) bringing an endoplasmic reticulum stressor and a test substance with the transformant of Item 7;
(h) measuring the fluorescence intensity of the transformant in contact with the endoplasmic reticulum stressor and the test substance, and comparing the measured fluorescence intensity with the fluorescence intensity of a control transformant that is not in contact with the test substance but in contact with the endoplasmic reticulum stressor; and
(i) selecting the test substance as an antidiabetic drug candidate when the fluorescence intensity of the transformant in contact with the endoplasmic reticulum stressor and the test substance is higher than the fluorescence intensity of the control transformant.

Advantageous Effects of Invention

The present invention is characterized by using a polynucleotide encoding a nonfluorescent peptide domain 1 derived from a fluorescent protein constituted of a nonfluorescent peptide domain 1 and a nonfluorescent peptide domain 2; and the ATF6 protein domain. The present invention having such a characteristic enables real-time evaluation of activation of the pathway mediated by ATF6 in viable cells with a high degree of sensitivity. More specifically, the screening method of the present invention enables determination as to whether a given substance or a given physiological/pathological environment serves as an endoplasmic reticulum stressor that activates the pathway mediated by ATF6. The screening method of the present invention further enables determination (screening) as to whether a test substance is an endoplasmic reticulum stress inhibitor that suppresses endoplasmic reticulum stress caused by activation of the pathway mediated by ATF6. Furthermore, the screening method of the present invention enables screening of an antidiabetic drug candidate.

Further, the screening method of the present invention makes it possible to, for the first time, perform evaluation of endoplasmic reticulum stress mediated by the three pathways (the three pathways individually mediated by IRE1α, PERK, and ATF6) involved in endoplasmic reticulum stress response simultaneously and in the same cells. Using this evaluation of the present invention, it was discovered that the degree of response to endoplasmic reticulum stress varies between the three pathways for each cell group derived from a different organ.

BRIEF DESCRIPTION OF DRAWINGS

FIG. 4 shows a DNA sequence (SEQ ID NO: 17) inserted in an EGFP-ATF6d expression vector.
1) green fluorescent protein cDNA fragment
2) spacer
3) 3XFLAG tag
4) nuclear localization signal
5) PEST sequence
6) partial cDNA fragment of mice ATF6α

FIG. 5 shows a DNA sequence (SEQ ID NO: 24) inserted in an EGFPL expression vector.
7) nuclear localization signal
8) green fluorescent protein cDNA fragment.

FIG. 9 shows a DNA sequence (SEQ ID NO: 27 and 28) used for production of an EGFP-ATF6d expression vector in which the spacer is changed to GGGS (SEQ ID NO: 5) or GGGSGGGSGGGS (SEQ ID NO: 6).

DESCRIPTION OF EMBODIMENTS (1) the Principle of the Present Invention

The principle of the present invention is described below in reference to FIGS. 2 and 3.

The fluorescent protein of the present invention is constituted of a nonfluorescent peptide domain 1 and a nonfluorescent peptide domain 2. The nonfluorescent peptide domain 1 and the nonfluorescent peptide domain 2 are derived from the same fluorescent protein, and correspond to two fragments obtained by dividing a fluorescent protein in the molecule. Accordingly, when the nonfluorescent peptide domain 1 is an N-terminus fragment, the nonfluorescent peptide domain 2 is a C-terminus fragment. Conversely, when the nonfluorescent peptide domain 1 is a C-terminus fragment, the nonfluorescent peptide domain 2 is an N-terminus fragment. The nonfluorescent peptide domains 1 and 2 do not independently have fluorescence activity; however, they exhibit fluorescence activity as they are associated in a cell.

Figure 1:
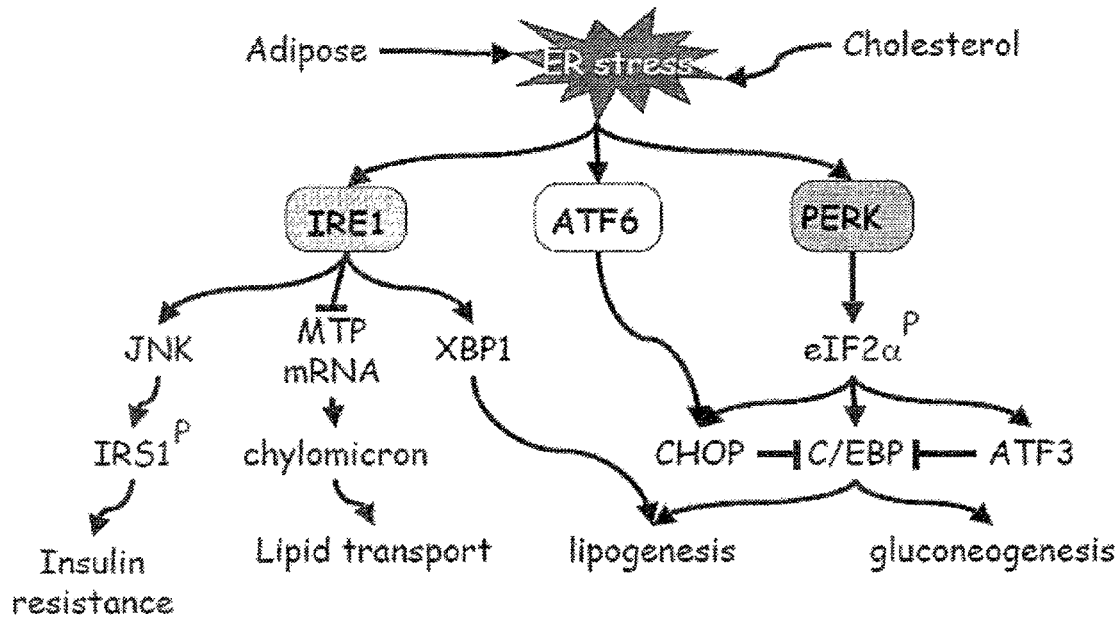
FIG. 1 shows three pathways activated by endoplasmic reticulum stress, and an example of an endoplasmic reticulum stress response caused by the activation of the three pathways.
Figure 2:
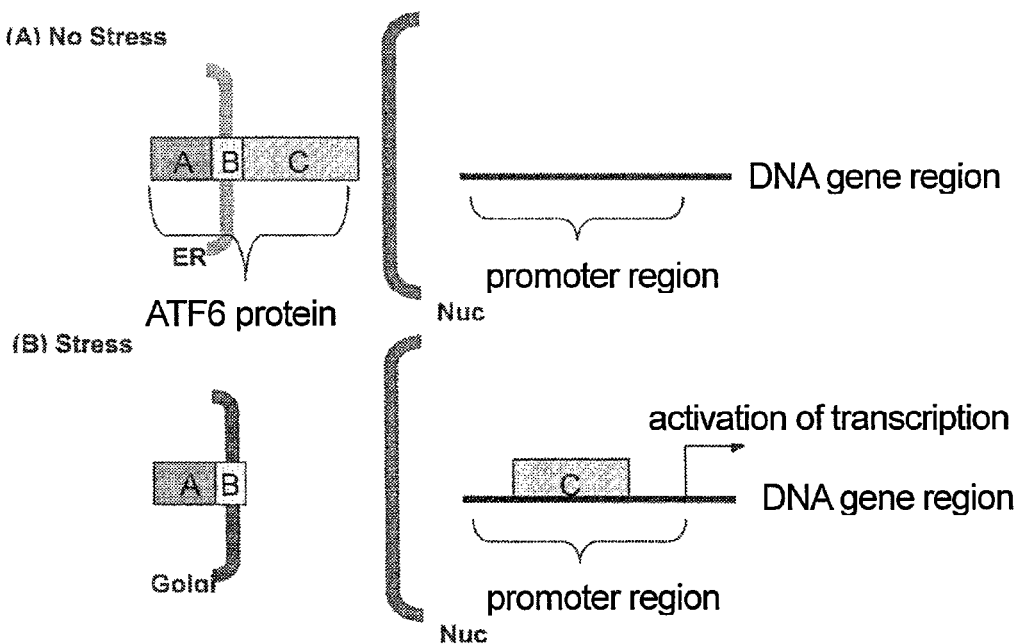
FIG. 2 shows a function of ATF6 protein in a cell. Panel (A) shows a function of ATF6 protein in a cell with no stress. Panel (B) shows a function of ATF6 protein in a cell with stress.
Figure 3:
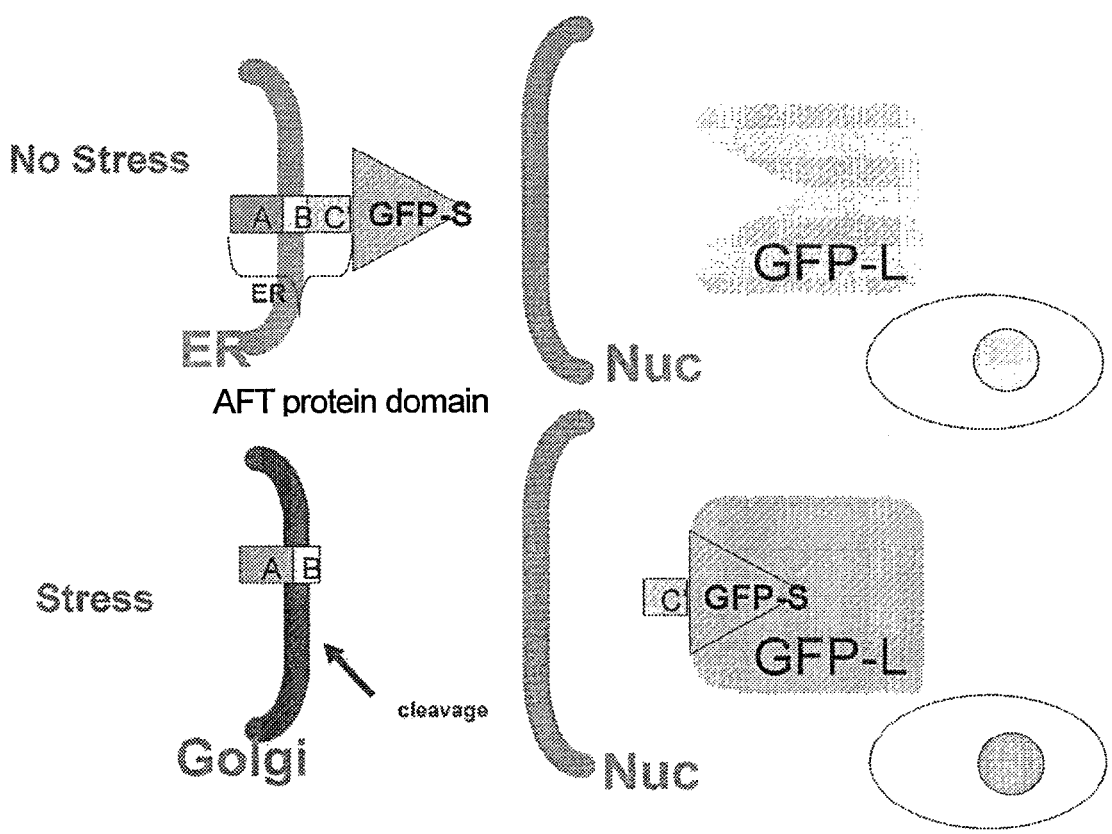
FIG. 3 shows a principle of the screening method of the present invention.

ATF6 protein is constituted of an endoplasmic reticulum lumen domain ("A" in FIG. 2), a transmembrane domain ("B" in FIG. 2), and a cytoplasmic domain ("C" in FIG. 2). ATF6 protein is present in a cell while penetrating the endoplasmic reticulum membrane ("ER" in FIG. 2). In response to endoplasmic reticulum stress that activates a pathway mediated by ATF6 protein, the part corresponding to the cytoplasmic domain of ATF6 protein ("C" in FIG. 2) is separated. The separated cytoplasmic domain ("C" in FIG. 2) is transferred to a nucleus ("Nuc" in FIG. 2) by a nuclear localization signal inherent in the domain, and serves as a transcription factor that adjusts the transcription of the gene group involved in the endoplasmic reticulum stress response. The present invention uses this mechanism to create a system for evaluating endoplasmic reticulum stress that activates the pathway mediated by ATF6. The evaluation system of the present invention operates as follows (see FIG. 3).

The fusion protein of the nonfluorescent peptide domain 1 derived from a fluorescent protein ("GFP-S" in FIG. 3; hereinafter referred to as "nonfluorescent peptide domain 1") expressed in a cell, and a ATF6 protein domain ("A," "B," and "C" in FIG. 3) is disposed on the endoplasmic reticulum membrane by the transmembrane domain ("B" in FIG. 3) of ATF6 protein domain. By this placement of the fusion protein, the endoplasmic reticulum lumen domain ("A" in FIG.

3) in the ATF6 protein domain is present in the endoplasmic reticulum lumen, and the nonfluorescent peptide domain 1 ("GFP-S" in FIG. 3), and the cytoplasmic domain ("C'" in FIG. 3) in the ATF6 protein domain are present in the cytoplasm.

Further, under the endoplasmic reticulum stress, the nonfluorescent peptide domain 1 ("GFP-S" in FIG. 3), and the cytoplasmic domain ("C'" in FIG. 3) in the ATF6 protein domain are cleaved from the endoplasmic reticulum membrane, and transferred into the nucleus by a nuclear localization signal in the ATF6 protein domain or a nuclear localization signal artificially introduced into the fusion protein.

The nonfluorescent peptide domain 1 ("GFP-S" in FIG. 3) in the fusion protein transferred into the nucleus is associated with the fluorescent protein-derived nonfluorescent peptide domain ("GFP-L" in FIG. 3) present in the same nucleus. By the association, the original fluorescence activity of the fluorescent protein recovers. The recovery of the fluorescence activity can be confirmed by the presence of fluorescence generated in response to irradiation of excitation light of a wavelength corresponding to the type of the fluorescent protein.

More specifically, the endoplasmic reticulum stress mediated by ATF6 can be evaluated by detecting a fluorescence.

(2) Polynucleotide of the Present Invention

The polynucleotide of the present invention is a polynucleotide encoding an amino acid sequence having a nonfluorescent peptide domain 1 derived from a fluorescent protein constituted of nonfluorescent peptide domain 1 and nonfluorescent peptide domain 2; and an ATF6 protein domain.

(2-1) Nonfluorescent Peptide Domain 1 of the Present Invention Derived from a Fluorescent Protein (Hereinafter Referred to as Nonfluorescent Peptide Domain 1 of the Present Invention)

The fluorescent protein is not particularly limited insofar as it loses the fluorescence activity by the division in the molecule, and gains the fluorescence activity again as the divided fragments are associated. Preferable examples of fluorescent proteins include GFP, GFP mutants, and a GFP-like protein family not derived from GFP. Among them, GFP and GFP mutants are particularly preferable. GFP is a green fluorescent protein derived from *Aequorea victoria*. The amino acid sequence of GFP is represented by amino acid SEQ ID NO: 4.

Further, the fluorescent protein may be modified by substitution, deletion, or addition of one or more amino acids insofar as it loses the fluorescence activity by the division in the molecule, and gains the fluorescence activity again as the divided fragments are associated.

As for the substitution, so as to maintain the protein structure, the amino acid may be substituted with an amino acid similar to the original amino acid (the amino acid before substitution) in terms of polarity, electric charge, solubility, hydrophilicity/hydrophobicity, polarity, and the like. According to the amino acid classification, glycine, alanine, valine, leucine, isoleucine, and proline are classified into nonpolar amino acids; serine, threonine, cysteine, methionine, asparagine, and glutamine are classified into polar amino acids; phenylalanine, tyrosine, and tryptophan are classified into amino acids having aromatic side chain; lysine, arginine, and histidine are classified into basic amino acids; and aspartic acid and glutamic acid are classified into acidic amino acids. The substitution is performed using a protein in the same protein group.

The GFP mutants are obtained by substituting at least one amino acid in GFP. By the substitution, a GFP mutant is modified in fluorescence intensity, excite wavelength, fluorescence wavelength, and stability in a cell. Examples of GFP mutants include EGFP, YFP, CFP, and RFP. The amino acid sequence of EGFP is represented by amino acid SEQ ID NO: 1.

The fluorescent protein, which belongs to the GFP-like protein family, has a structure similar to GFP (having a helix tissue of eleven β-sheets, which further forms a cylindrical structure by covering the chromophore (white portion). Examples of fluorescent proteins include CopGFP derived from crustaceans, and DsRed derived from sea anemone.

Various examples of GFP mutants and fluorescent proteins belonging to the GFP-like protein family are disclosed in published documents, including Document 1 (Appl. Microbiol. Biotechnol. (2007) 77:1-12.

The nonfluorescent peptide domain 1 of the present invention is an N-terminus fragment or a C-terminus fragment obtained by dividing a fluorescent protein in the molecule. The division site is not limited insofar as the division deactivates the fluorescence activity of each fragment (the N-terminus fragment and the C-terminus fragment) and the fluorescence activity is recovered by the reunion of the two divided fragments. The division site can be determined by referring to published documents, including Document 2 (Nature Biotechnology, 2003, vol. 21, 539-545). For example, for EGFP, the division site is preferably one of the 195th to 226th amino acids in SEQ ID NO: 1, more preferably one of the 205th to 222nd amino acids in SEQ ID NO: 1, particularly preferably one of the 212th to 218th amino acids in SEQ ID NO: 1. Further, in these examples, it is preferable to use a C-terminus fragment as the nonfluorescent peptide domain 1 of the present invention.

(2-2) ATF6 Protein Domain of the Present Invention

The biological species to be used to obtain ATF6 protein include not only mice (*Mus musculus*), but also other biological species having a genomic region encoding ATF6 protein having an amino acid sequence identity of preferably not less than 70%, more preferably not less than 80%, further preferably not less than 85%, further more preferably not less than 90%, particularly preferably not less than 95% with the mice ATF6 protein. Examples of such biological species include rodents such as rats; and mammals such as rabbit, apes, and humans (*Homo sapiens*). Humans (*Homo sapiens*) and mice (*Mus musculus*) are most preferable biological species.

ATF6 protein is constituted of a cytoplasmic domain, an endoplasmic reticulum transmembrane domain, and an endoplasmic reticulum lumen domain. When the biological species is a mouse, ATF6 protein has an amino acid sequence of SEQ ID NO: 2, or an amino acid sequence having an identity of not less than 90%, preferably not less than 95%, more preferably not less than 98% with the amino acid sequence of SEQ ID NO: 2. When the biological species is a human, the ATF6 protein has an amino acid sequence of SEQ ID NO: 3, or an amino acid sequence having an identity of not less than 90%, preferably not less than 95%, more preferably not less than 98% with the amino acid sequence of SEQ ID NO: 3. When the biological species is a mouse, a region of the 1st to 364th amino acids in the amino acid sequence of SEQ ID NO: 2 corresponds to the cytoplasmic domain, a region of the 365th to 384th amino acids in the amino acid sequence of SEQ ID NO: 2 corresponds to the endoplasmic reticulum transmembrane domain, and a region of the 385th to 656th amino acids in the amino acid sequence of SEQ ID NO: 2 corresponds to the endoplasmic reticulum lumen domain. When the biological species is a human, a region of the 1st to 377th amino acids in the amino acid sequence of SEQ ID NO: 3 corresponds to the cytoplasmic domain, a region of the 378th to 398th amino acids in the amino acid sequence of SEQ ID NO: 3 corresponds to the endoplasmic reticulum transmembrane domain, and a region of the 399th to 670th amino acids in the amino acid sequence of SEQ ID NO: 3 corresponds to the endoplasmic reticulum lumen domain.

The ATF6 protein domain of the present invention includes a nuclear localization signal peptide region (a nuclear localization signal peptide in ATF6 protein and/or an exogenous nuclear localization signal peptide), a region involved in the division by endoplasmic reticulum stress, an endoplasmic reticulum transmembrane domain, and a portion receiving endoplasmic reticulum stress in the endoplasmic reticulum lumen domain. Insofar as it is within the above-listed domains, the ATF6 protein domain may be the entire length of the ATF6 protein.

The nuclear localization signal in the ATF6 protein is represented by the amino acid sequence RKKKKE (SEQ ID NO: 7). When the biological species is a mouse, the nuclear localization signal corresponds to a region of the 311th to 316th amino acids in the amino acid sequence of SEQ ID NO: 2. When the biological species is a human, the nuclear localization signal corresponds to a region of the 324th to 329th amino acids in the amino acid sequence of SEQ ID NO: 3.

A hitherto-known signal peptide, such as DPKKKRKV (SEQ ID NO: 8), may be used as the exogenous nuclear localization signal peptide. The nuclear localization signal peptide may also be a repetition of the sequence of a hitherto-known signal peptide.

The portion receiving endoplasmic reticulum stress in the endoplasmic reticulum lumen domain is a region that receives endoplasmic reticulum stress and causes the division of the ATF6 cytoplasmic domain.

The region involved in the division by endoplasmic reticulum stress is a region of the 365th to 411th amino acids in the amino acid sequence of SEQ ID NO: 2 when the biological species is a mouse, and is a region of the 378th to 424th amino acids in the amino acid sequence of SEQ ID NO: 3 when the biological species is a human.

The ATF6 protein domain of the present invention is not limited insofar as the domain has the nuclear localization signal peptide region (a nuclear localization signal peptide in ATF6 protein and/or an exogenous nuclear localization signal peptide), the region involved in the division by endoplasmic reticulum stress, the endoplasmic reticulum transmembrane domain, and the portion receiving endoplasmic reticulum stress in the endoplasmic reticulum lumen domain. However, when the biological species is a mouse, the ATF6 protein domain of the present invention is a domain having a region of the 100th to 656th amino acids in the ATF6 protein amino acid sequence of SEQ ID NO: 2, or an amino acid region having an amino acid identity of not less than 90%, preferably not less than 95%, more appropriately not less than 98% with the above amino acid region; more preferably, the ATF6 protein domain is a domain having a region of the 250th to 656th amino acids in the ATF6 protein amino acid sequence of SEQ ID NO: 2, or an amino acid region having an amino acid identity of not less than 90%, preferably not less than 95%, more preferably not less than 98% with the above amino acid region; particularly preferably, the ATF6 protein domain is a domain having an exogenous nuclear localization signal peptide region and a region of the 360th to 656th amino acids in the ATF6 protein amino acid sequence of SEQ ID NO: 2, or an amino acid region having an amino acid identity of not less than 90%, preferably not less than 95%, more preferably not less than 98% with the above amino acid region. When the biological species is a human, the ATF6 protein domain of the present invention is preferably a domain having a region of the 100th to 670th amino acids in the ATF6 protein amino acid sequence of SEQ ID NO: 3, or an amino acid region having an amino acid identity of not less than 90%, preferably not less than 95%, more preferably not less than 98% with the above amino acid region; more preferably, the ATF6 protein domain is a domain having a region of the 250th to 670th amino acids in the amino acid sequence of SEQ ID NO 3, or an amino acid region having an amino acid identity of not less than 90%, preferably not less than 95%, more preferably not less than 98% with the above amino acid region; particularly preferably, the ATF6 protein domain is a domain having an exogenous nuclear localization signal peptide region and a region of the 373rd to 670th amino acids in the ATF6 protein amino acid sequence of SEQ ID NO: 3, or an amino acid region having an amino acid identity of not less than 90%, preferably not less than 95%, more preferably not less than 98% with the above amino acid region.

The ATF6 protein domain may be a domain resulting from substitution, deletion, or addition of one or more amino acids in the above-listed domain examples. Such a mutation may be suitably conducted insofar as the functions of the nuclear localization signal peptide region, the portion receiving endoplasmic reticulum stress in the endoplasmic reticulum lumen domain, the endoplasmic reticulum transmembrane domain, and the portion divided by endoplasmic reticulum stress in the cytoplasmic domain are obtained.

As for the substitution, so as to maintain the protein structure, the amino acid may be substituted with an amino acid similar to the original amino acid (the amino acid before substitution) in terms of polarity, electric charge, solubility, hydrophilicity/hydrophobicity, polarity, and the like. According to the amino acid classification, glycine, alanine, valine, leucine, isoleucine, and proline are classified into nonpolar amino acids; serine, threonine, cysteine, methionine, asparagine, and glutamine are classified into polar amino acids; phenylalanine, tyrosine, and tryptophan are classified into amino acids having an aromatic side chain; lysine, arginine, and histidine are classified into basic amino acids; and aspartic acid and glutamic acid are classified into acidic amino acids. The substitution is performed using a protein in the same protein group.

(2-3) Dispositions of Nonfluorescent Peptide Domain 1 and ATF6 Protein Domain

In the present invention, the locations of the two domains in the polynucleotide encoding the nonfluorescent peptide domain 1 and the ATF6 protein domain are not particularly limited. However, it is preferable that the region encoding the nonfluorescent peptide domain 1 is located at the 5' end, and that the region encoding the ATF6 protein domain is located at the 3' end.

Further, the nonfluorescent peptide domain 1 derived from a fluorescent protein and the ATF6 protein domain are preferably disposed having a spacer therebetween.

The spacer used in the present invention designates an amino acid sequence derived from a natural protein or a synthetic amino acid sequence. Although the amino acid sequence of the spacer is not particularly limited, the sequence is preferably an amino acid sequence that does not form a secondary structure, such as the α-helix structure or the β-sheet structure; and that can be freely folded. Examples of the amino acid sequence of the spacer include the four residues GGGS, and a repetition of this sequence.

The number of the amino acid residues of the spacer is preferably not less than 3, more preferably 4 to 50, further preferably 6 to 20, particularly preferably 7 to 15. In the present invention, if the number of amino acid residues of the spacer is too small, the association of the nonfluorescent peptide domains 1 and 2 derived from a fluorescent protein is assumed to be hindered by the ATF6 protein domain; and the desired fluorescence detection sensitivity in the method for screening an endoplasmic reticulum stressor, an endoplasmic reticulum stress inhibitor, or an antidiabetic drug candidate using the polynucleotide of the present invention is not ensured.

(2-4) Other Sequences

The polynucleotide of the present invention may contain other sequences including a polynucleotide encoding a protein tag, and polynucleotides encoding other peptides.

FLAG tag, His tag, GST tag, and the like, may be used as the protein tag. The protein tag may also be a repetition of the above tag sequence.

Other examples of peptide include PEST sequences. Insertion of a PEST sequence promotes degradation of the fusion protein. The PEST sequence is not particularly limited, and hitherto-known PEST sequences may be used insofar as the desired function is ensured. Examples thereof include the amino acid sequence of SHGFPPEVEEQDDGTLPMSCAQESGMDRHPAACASARINV (SEQ ID NO: 9). The location of the PEST sequence is not particularly limited insofar as the desired function is ensured; however, the PEST sequence is preferably disposed between the nonfluorescent peptide domain 1 and the ATF6 protein domain. Although the PEST sequence is not indispensable in the present invention, the insertion of a PEST sequence reduces the background fluorescence during the method for screening an endoplasmic reticulum stressor, an endoplasmic reticulum stress inhibitor, or an antidiabetic drug candidate using the polynucleotide of the present invention, thereby enabling fluorescence detection with a high degree of sensitivity.

(3) Production Method of Polynucleotide of the Present Invention

The polynucleotide of the present invention can be synthesized through artificial gene synthesis, or nucleic acid amplification (PCR, etc.) using a commercially available polynucleotide or a polynucleotide from a cDNA library. The polynucleotides encoding the above domains may be connected through a hitherto-known gene linkage technology by adding a hitherto-known restriction enzyme sequence at both ends.

Various expression vectors having a polynucleotide encoding a fluorescent protein are commercially available (for example, products of Clontech). The sequence data of the polynucleotide is also published.

The polynucleotide encoding the ATF6 protein domain can be obtained, for example, by creating a primer of an appropriate site based on the ATF6 gene sequence published in the NCBI database or other gene databases, and producing a polynucleotide through a gene amplification technology using a corresponding primer obtained from a cDNA library.

The other sequences inserted in the polynucleotide of the present invention, such as the polynucleotide sequence encoding a protein tag, the polynucleotide sequence encoding a nuclear localization signal, or the polynucleotide sequence encoding a PEST sequence, are open to the public. Therefore, these sequences can be obtained, for example, using artificial gene synthesis technology by referring to published sequence data.

(4) Transgenic Vector of the Present Invention

The transgenic vector of the present invention is a transgenic vector containing the polynucleotide of the present invention, and can be obtained by connecting the polynucleotide of the present invention to an appropriate vector.

The vector is not particularly limited insofar as it contains the polynucleotide of the present invention; however, the vector is preferably capable of enabling expression of the fusion protein resulting from the polynucleotide of the present invention in eukaryote cells, more preferably in animal cells, further preferably in mammal animal cells, particularly preferably in rodent (in particular, mice) or human cells. Specific examples of vectors include Escherichia coli vectors pBR322, pUC19, pKK233-2, pET21a, and the like; yeast vectors Yip5, Yrp17, Yep24, and the like; and animal cell vectors pcDNA, pBAC, and the like.

The above transgenic vector preferably contains a marker gene to enable selection of the transformed cells. Examples of marker genes include genes for complementing auxotrophy of the host, or drug-resistant genes. Further, the transgenic vector preferably also contains a promoter or other control sequences (for example, an enhancer sequence, a terminator sequence, a polyadenylation sequence, and the like) for enabling expression of the above genes in the host. Examples of promoters include SV40, CMV, ie1, T7, lac, trp, and tac.

(5) Transformant of the Present Invention

A transformant containing the above transgenic vector can be obtained by transforming a host using the transgenic vector.

The host is not particularly limited insofar as it is transformable by the transgenic vector of the present invention. Examples of hosts include cells such as Escherichia coli, yeasts, filamentous fungi, and animal cells. Among them, it is preferable to use eukaryote cells, more preferably animal cells, and further preferably rodent (in particular, mice) or human cells. Further, when the host is animal cells, the host cells may be obtained from various organs including pancreatic cells, kidney cells, hepatic cells, adipose cells, and skeletal cells. When the transformant is used for the method for screening an antidiabetic drug candidate, the host cells are preferably pancreatic cells. Among pancreatic cells, pancreatic β-cells are more preferable.

The transformation may be performed using a hitherto-known method according to the type of the host. Examples of the hitherto-known methods include a calcium chloride method, electroporation method, lipofection method, and DEAF dextran method. The transformant of the present invention may be selected from the thus-obtained transformants based on a drug resistance marker, etc., of the vector.

Further, the transformant of the present invention preferably contains a polynucleotide encoding an amino acid sequence having a nonfluorescent peptide domain 2 derived from a fluorescent protein constituted of a nonfluorescent peptide domain 1 and a nonfluorescent peptide domain 2 (hereinafter, the domain referred to as "nonfluorescent peptide domain 2" designates this protein), and a nuclear localization signal peptide domain while ensuring a condition where the protein having the amino acid sequence can be expressed. This transformant (hereinafter referred to as "screening transformant") may be used for the later-described screening method. Further, a screening transformant obtained by using pancreatic β-cells as the host (hereinafter referred to as "antidiabetic drug candidate screening transformant") may be suitable for the later-described screening method, in particular, the method for screening antidiabetic drug candidates.

The nonfluorescent peptide domain 2 is an N-terminus fragment or a C-terminus fragment generated by dividing a fluorescent protein in the molecule. The nonfluorescent peptide domain 2 is obtained from the same fluorescent protein from which the aforementioned nonfluorescent peptide domain 1 is obtained. The nonfluorescent peptide domains 1 and 2 correspond to the two fragments resulting from the division of a fluorescent protein. Therefore, when the nonfluorescent peptide domain 1 is an N-terminus fragment, the nonfluorescent peptide domain 2 is a C-terminus fragment.

The N-terminus fragment and the C-terminus fragment can be arbitrarily used as the nonfluorescent peptide domain 1 or 2. However, it is preferable that the nonfluorescent peptide domain 1 be a C-terminus fragment, and that the nonfluorescent peptide domain 2 be an N-terminus fragment.

A hitherto-known signal peptide, such as Asp-Pro-Lys-Lys-Lys-Arg-Lys-Val (SEQ ID NO: 8), may be used as the nuclear localization signal peptide domain. The nuclear localization signal peptide domain may also be a repetition of a sequence of a hitherto-known signal peptide.

The state where "the protein can be expressed" is not particularly limited insofar as the protein constituted of an amino acid sequence containing the nonfluorescent peptide domain 2, and the nuclear localization signal peptide domain can be expressed in the cells. However, the 5' end of the polynucleotide encoding an amino acid sequence having a nonfluorescent peptide domain 2 and a nuclear localization signal peptide domain preferably has a promoter sequence.

A hitherto-known sequence may be used as the promoter sequence. Examples of the promoter sequence include CMV promoter sequence, SV40 promoter, and the like.

(6) the Screening Method of the Present Invention

Using the above transformant, it is possible to screen an endoplasmic reticulum stressor, an endoplasmic reticulum stress inhibitor, or an antidiabetic drug candidate.

(6-1) A Method for Screening Endoplasmic Reticulum Stressor

The method for screening an endoplasmic reticulum stressor includes a step of (a) bringing an endoplasmic reticulum stressor candidate substance into contact with the screening transformant described in "(5) Transformant of the Present Invention"; a step of (b) measuring the fluorescence intensity of the transformant in contact with the endoplasmic reticulum stressor candidate substance, and comparing the measured fluorescence intensity with the fluorescence intensity of a control transformant not in contact with the endoplasmic reticulum stressor candidate substance; and a step of (c) selecting the endoplasmic reticulum stressor candidate substance as an endoplasmic reticulum stressor when the fluorescence intensity of the transformant in contact with the endoplasmic reticulum stressor candidate substance is higher than the fluorescence intensity of the control transformant.

The type of the substance as a candidate for endoplasmic reticulum stressor is not particularly limited. Examples of candidates include proteins, peptides, non-peptidic compounds (nucleotides, amines, saccharides, lipids, etc.), organic low-molecular-weight compounds, inorganic low-molecular-weight compounds, fermentation products, cell extracts, plant extracts, and animal tissue extracts.

The step of bringing the endoplasmic reticulum stressor candidate substance into contact with the cells may be performed under conditions (in terms of temperature, pH, components of culture medium) in which the cells are kept alive and the fusion protein of the nonfluorescent peptide domain 1 derived from a fluorescent protein and the ATF6 protein domain, and the protein containing a nonfluorescent peptide domain 2 derived from a fluorescent protein can be expressed from the introduced transgenic vector. The concentration of the endoplasmic reticulum stressor candidate substance to be brought into contact with the cells varies depending on the type of the substance. For example, the concentration is about 0.001 to 100 μg/ml.

The fluorescence detection may be performed by generating fluorescence by emission of excitation light having a wavelength suitable for a fluorescent protein.

The method for measuring the fluorescence intensity is not particularly limited insofar as it enables comparison of the fluorescence intensity of the transformant in contact with the endoplasmic reticulum stressor with the fluorescence intensity of the control transformant not in contact with the endoplasmic reticulum stressor. For example, the fluorescence intensity measurement may be performed by capturing an image of the fluorescing transformant into a computer, and determining a color depth corresponding to the fluorescence in the image.

Further, screening of an organ-specific endoplasmic reticulum stressor becomes possible by using the transformant of the present invention derived from the target organ. For example, screening of a liver-specific endoplasmic reticulum stressor may be performed using a transformant of the present invention that is obtained using hepatic cells as the host.

Furthermore, by combining the screening method of the present invention with a hitherto-known screening method, it is possible to determine whether the endoplasmic reticulum stressor is:

an endoplasmic reticulum stressor that activates ATF6 pathway, but does not activate IRE1α pathway or PERK pathway;
an endoplasmic reticulum stressor that activates ATF6 pathway, IRE1α pathway, and/or PERK pathway; or
an endoplasmic reticulum stressor that does not activate ATF6 pathway, but activates IRE1α pathway and/or PERK pathway.

More specifically, it is possible to determine whether the endoplasmic reticulum stressor is:

(o) an endoplasmic reticulum stressor that activates ATF6 pathway, but does not activate IRE1α pathway or PERK pathway;
(p) an endoplasmic reticulum stressor that activates ATF6 pathway and IRE1α pathway, but does not activate PERK pathway;
(q) an endoplasmic reticulum stressor that activates ATF6 pathway and PERK pathway, but does not activate IRE1α pathway;
(r) an endoplasmic reticulum stressor that activates ATF6 pathway, IRE1α pathway, and PERK pathway;
(s) an endoplasmic reticulum stressor that does not activate ATF6 pathway, but activates IRE1α pathway and PERK pathway;
(t) an endoplasmic reticulum stressor that does not activate ATF6 pathway and IRE1α pathway, but activates PERK pathway; or
(u) an endoplasmic reticulum stressor that does not activate ATF6 pathway and PERK pathway, but activates IRE1α pathway.

The hitherto-known screening method is a method capable of selecting whether the endoplasmic reticulum stressor candidate substance activates IRE1α pathway and/or PERK pathway. For example, the method disclosed in JP2005-204516A may be used. Therefore, by combining such a hitherto-known screening method with the method of the present invention capable of screening an endoplasmic reticulum stressor that activates ATF6 pathway from multiple endoplasmic reticulum stressor candidate substances, it becomes possible to determine which of the endoplasmic reticulum stressors (o) to (u) corresponds to the endoplasmic reticulum stressor activating ATF6 pathway. Further, the combination of the method of the present invention with the hitherto-known screening method also enables screening of an endoplasmic reticulum stressor that does not activate ATF6 pathway.

The method disclosed in JP2005-204516A is specifically described below.

The cells used in this method are transgenic cells containing:

(v) an expression vector containing a fusion gene of XBP1 gene and a gene encoding a first reporter protein; the expression vector being disposed so that the fusion protein of XBP1 protein and the first reporter protein is expressed only when XBP1 gene is spliced; and (w) an expression vector containing a fusion gene of ATF4 gene and a gene encoding a second reporter protein; the gene encoding the second reporter protein being disposed downstream of the true translation start point of ATF4 gene.

Using the above transgenic cells, it is possible to select whether a candidate substance is an endoplasmic reticulum stressor that activates IRE1α pathway and/or PERK pathway through the following method including:

(x) a step of bringing the transgenic cells into contact with a candidate substance, (y) a step of measuring the activities of the first reporter protein and the second reporter protein in the transgenic cells; and (z) a step of, in the transgenic cell, determining the candidate substance as an endoplasmic reticulum stressor that activates IRE1α pathway but does not activates PERK pathway when the activity of the first reporter protein is detected and the activity of the second reporter protein is not detected; and when the activity of the first reporter protein is not detected and the activity of the second reporter protein is detected, determining the candidate substance as an endoplasmic reticulum stressor that activates PERK pathway and does not activate IRE1α pathway; and when the activities of the first reporter protein and the second reporter protein are both detected, determining the candidate substance as an endoplasmic reticulum stressor that activates IRE1α pathway and PERK pathway.

Gene for ERAI System

Figure 17:
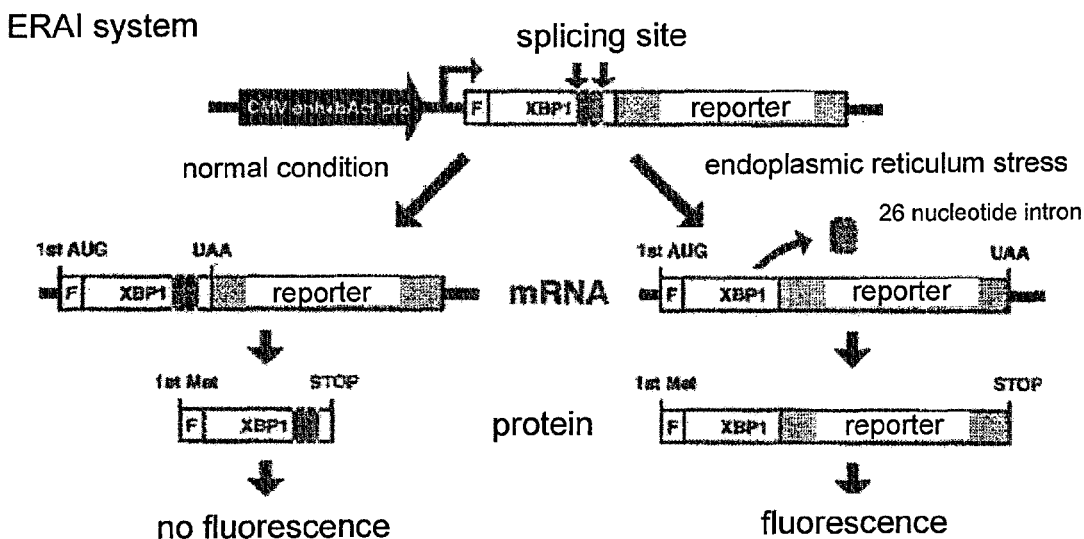
FIG. 17 shows a gene architecture in ERAI system, and a mechanism of ERAI system.
Figure 18:
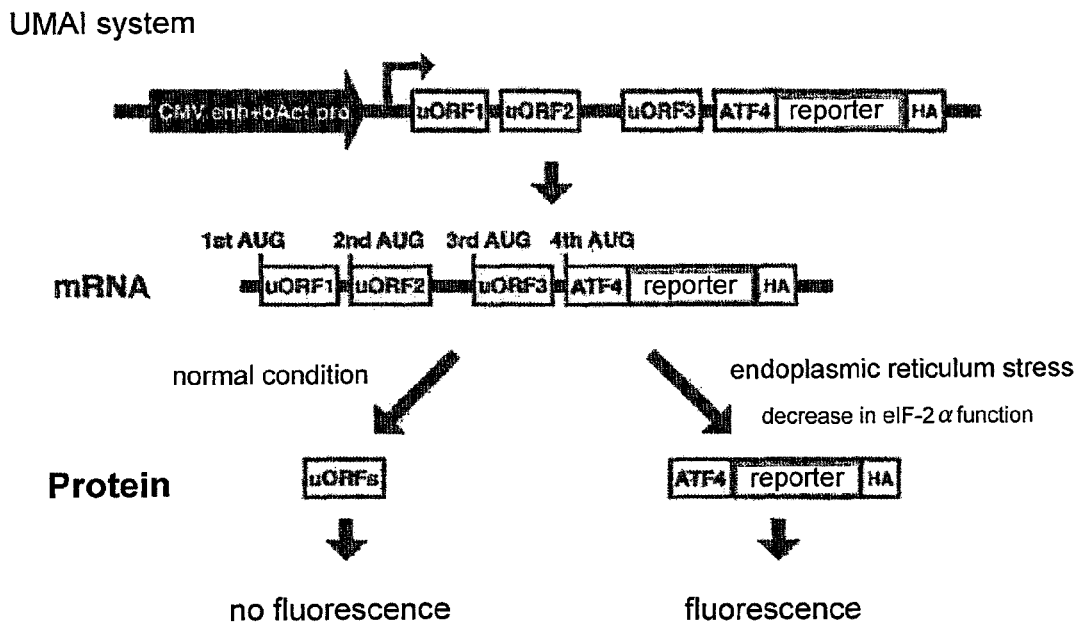
FIG. 18 shows a gene architecture in UMAI system, and a mechanism of UMAI system.

As shown in FIG. 17, the expression vector (v) is structured to activate the ERAI system. The expression vector (v) contains a fusion gene of XBP1 gene and a gene encoding the first reporter protein, and is disposed so that the fusion protein of XBP1 protein and the first reporter protein is expressed only when XBP1 gene is spliced.

XBP1 gene is one of the stimulus response genes. Under endoplasmic reticulum stress, IRE1 splices a 26 nucleotide intron of XBP1. Examples of known cDNA sequences of XBP1 include XBP1 of human, bovine, mice, *Xenopus laevis*, and zebra fish. They are registered in the EST database as BE170119, AV604667, BF143019, AF358133, and AF399918, respectively. In the present invention, cDNA of human XBP1 (hereinafter referred to as "Sequence 1"), NCBI registration No. AB076383, is used as an example of cDNA of XBP1. During the absence of splicing, the positions 9 to 794 of Sequence 1 serve as a code-coding region, and are translated into an XBP1 protein (truncated protein) having 261 amino acid residues (hereinafter referred to as "Sequence 2"). On the other hand, the intron of cDNA corresponds to a base sequence at positions 50 to 527 of Sequence 1. The splicing of XBP1 gene by IRE1 results in a frameshift that allows positions 9 to 501 and 528 to 1165 of Sequence 1 to serve as a coding region, thus translating XBP1 into an active XBP1 protein having 376 amino acid residues.

The gene encoding the first reporter protein is fused to an appropriate position in the downstream of the active XBP1 protein coding region expressed by splicing while ensuring accordance of the reading frame. More specifically, expression vector (v) is structured such that the fusion protein of the active XBP1 protein and the first reporter protein is expressed only by the splicing by IRE1.

The first reporter protein is not particularly limited insofar as its expression can be confirmed. A protein having a fluorescence activity is preferable in terms of easy confirmation in vivo. Examples of proteins having a fluorescence activity include luciferase, green fluorescent protein (GFP), and mutants thereof. Examples of luciferase include firefly luciferase, and Renilla luciferase. Examples of green fluorescent proteins and mutants thereof include *Aequorea victoria* green fluorescent protein, EGFP (enhanced green fluoro protein), YFP (yellow fluoro protein), BFP (blue fluoro protein), and RFP (red fluoro protein). They are all commercially available, and can be easily obtained.

Gene for UMAI System

The expression vector (w) has a fusion gene of ATF4 gene and the gene encoding the second reporter protein. The gene encoding the second reporter protein is located in the downstream of the true translation start point of the ATF4 gene.

Under endoplasmic reticulum stress, PERK is activated, and eIF-2α is phosphorylated. As a result, the function of eIF-2α decreases, thereby promoting the translation from the true translation start point, which is located undermost in the stream, among the multiple translation start points in mRNA of ATF4. Examples of known cDNA sequences of ATF4 include ATF4 of human, mice, and Aplysia. They are published in the EST database as HSU03712, NM_009716, and ACU40851, respectively. In the present invention, cDNA of human ATF4 (hereinafter referred to as "Sequence 3"), NCBI registration No. BC011994, is used as cDNA of ATF4. After the transcription by mRNA, under a normal condition, i.e., when eIF-2α normally functions, cDNA of ATF4 is translated from the false multiple upstream translation start point. More specifically, the positions 4 to 9, 67 to 78, and 166 to 345 of Sequence 3 are translated. On the other hand, upon activation of PERK, positions 263 to 1318 in Sequence 3, which is the true translation start point of mRNA of ATF4, are translated.

The gene encoding the second reporter protein is located in the downstream of the true translation start point of ATF4 gene. For example, regarding cDNA of human ATF4 having NCBI registration No. HSU03712, the gene encoding the second reporter protein is located downstream of position 263 of Sequence 3, more specifically, downstream of the true translation initiation codon (positions 263 to 265 in SEQ ID NO: 5). Accordingly, only when the translation starts from the true translation start point in response to the activation of PERK is the second reporter protein expressed.

As with the first reporter protein, the second reporter protein is not particularly limited insofar as its expression can be confirmed. A protein having a fluorescence activity is preferably used as the second reporter protein in terms of easy confirmation in vivo. However, the second reporter protein must be a different protein from the first reporter protein so that its expression can be easily distinguished from the expression of the first reporter protein. Examples of the combination of the first reporter protein and the second reporter protein include a combination of a firefly luciferase and a Renilla luciferase, and a combination of EGFP and RFP.

With transgenic cells containing the expression vectors (v) and (w), the cells are cultured under appropriate conditions, for example, in an appropriate culture medium generally selected by a person skilled in the art. Then, the cells are brought into contact with a drug to be screened. The step of bringing the cells into contact with a drug may be performed by, for example, adding the drug in the culture medium, injecting the drug into the cells, or the like. After keeping the cells in contact with the drug for a predetermined duration, the expressions of the first reporter protein and the second reporter protein are measured. Usually, the expressions are measured by measuring the activities of the expressed proteins. For example, when the reporter protein is a fluorescent protein, the fluorescence intensity of the cells is measured.

If only the first reporter protein shows an increase in activity, it indicates that only IRE1α pathway is activated. Conversely, if only the second reporter protein shows an increase in activity, it indicates that only PERK pathway is activated. Further, if the increase in activity was observed in both the first and second reporter proteins, it indicates that both IRE1α pathway and PERK pathway are activated. If the increase in activity was not observed in either the first or second reporter protein, it indicates that neither IRE1α pathway nor PERK pathway are activated.

The combination of the screen method of the present invention and a hitherto-known screening method is not particularly limited. The following combinations are possible.

Instead of the screening transformant used in the example described in "(5) Transformant of the Present Invention," a transformant (hereinafter referred to as "transformant for 3-pathway detection") obtained by further adding the expression vectors (v) and (w) to the above transformant may be used. Here, the fluorescent protein and the first and second reporter proteins are selected in view of secure differentiation between the fluorescence intensity of the fluorescent protein used for the present screening method, the fluorescence intensity or activity of the first reporter protein, and the fluorescence intensity or activity of the second reporter protein. By bringing the transformant for 3-pathway detection into contact with an endoplasmic reticulum stressor candidate substance, and then comparing the test cells with the control cells in terms of the fluorescence intensity of the fluorescent protein and the fluorescence intensity or activity of the reporter proteins, it is possible to determine which of the aforementioned endoplasmic reticulum stressors (o) to (u) corresponds to the candidate substance.

The present screening method enables discovery of a substance that causes endoplasmic reticulum stress, and is thus useful for research regarding the mechanism of endoplasmic reticulum stress; or research regarding the treatment of diabetes or neurodegenerative disorders caused by endoplasmic reticulum stress.

(6-2) a Method for Screening Endoplasmic Reticulum Stress Inhibitor

A method for screening an endoplasmic reticulum stress inhibitor includes a step of (d) bringing an endoplasmic reticulum stressor and a test substance with the screening transformant used in the example described in "(5) Transformant of the Present Invention"; a step of (e) measuring the fluorescence intensity of the transformant in contact with the endoplasmic reticulum stressor and the test substance; and comparing the measured fluorescence intensity with the fluorescence intensity of a control transformant that is not in contact with the test substance, but in contact with the endoplasmic reticulum stressor; and a step of (f) selecting the test substance as an endoplasmic reticulum stress inhibitor when the fluorescence intensity of the transformant in contact with the endoplasmic reticulum stressor and the test substance is higher than the fluorescence intensity of the control transformant.

The endoplasmic reticulum stressor is not particularly limited insofar as it is a substance that causes endoplasmic reticulum stress. Examples of such substances include tunicamycin, thapsigargin, and DTT (dithiothreitol). Further, the endoplasmic reticulum stressor screened by the above method for screening endoplasmic reticulum stressor may also be used.

The type of the test substance is not particularly limited. Examples of the test substances include proteins, peptides, non-peptidic compounds (nucleotides, amines, saccharides, lipids, etc.), organic low-molecular-weight compounds, inorganic low-molecular-weight compounds, fermentation products, cell extracts, plant extracts, and animal tissue extracts.

The step of bringing the test substance into contact with the cells may be performed under conditions (in terms of temperature, pH, components of culture medium) in which the cells are kept alive and the fusion protein of the nonfluorescent peptide domain 1 derived from a fluorescent protein and the ATF6 protein domain, and the protein containing a nonfluorescent peptide domain 2 derived from a fluorescent protein can be expressed from the introduced transgenic vector. The concentration of the endoplasmic reticulum stressor candidate substance to be brought into contact with the cells varies depending on the type of the substance. For example, the concentration is about 0.001 to 100 μg/ml.

Further, screening of an organ-specific substance for suppressing endoplasmic reticulum stress becomes possible by using the transformant of the present invention derived from the target organ. For example, screening of a liver-specific substance for suppressing endoplasmic reticulum stress may be performed using the transformant of the present invention derived from hepatic cells.

The present screening method enables screening of a substance for suppressing endoplasmic reticulum stress, and thus is useful for research regarding the treatment of diabetes or neurodegenerative disorders caused by endoplasmic reticulum stress.

(6-3) A Method for Screening Antidiabetic Drug Candidate

A method for screening an antidiabetic drug candidate includes a step of (g) bringing an endoplasmic reticulum stressor and a test substance with the antidiabetic drug candidate screening transformant used in the example described in "(5) Transformant of the Present Invention"; a step of (h) measuring the fluorescence intensity of the transformant in contact with the endoplasmic reticulum stressor and the test substance, and comparing the measured fluorescence intensity with the fluorescence intensity of a control transformant that is not in contact with the test substance, but that is in contact with the endoplasmic reticulum stressor; and a step of (i) selecting the test substance as an antidiabetic drug candidate when the fluorescence intensity of the transformant in contact with the endoplasmic reticulum stressor and the test substance is higher than the fluorescence intensity of the control transformant.

The endoplasmic reticulum stressor is not particularly limited insofar as it is a substance that causes endoplasmic reticulum stress. Examples of such substances include tunicamycin, thapsigargin, and DTT. Further, the endoplasmic reticulum stressor screened by the above method for screening endoplasmic reticulum stressor may also be used.

The type of the test substance is not particularly limited. Examples of the test substances include proteins, peptides, non-peptidic compounds (nucleotides, amines, saccharides, lipids, etc.), organic low-molecular-weight compounds, inorganic low-molecular-weight compounds, fermentation products, cell extracts, plant extracts, and animal tissue extracts.

The step of bringing the test substance into contact with the cells may be performed under conditions (in terms of temperature, pH, components of culture medium) in which the cells are kept alive and the fusion protein of the nonfluorescent peptide domain 1 derived from a fluorescent protein and the ATF6 protein domain, and the protein containing a nonfluorescent peptide domain 2 derived from a fluorescent protein can be expressed from the introduced transgenic vector.

The concentration of the endoplasmic reticulum stressor candidate substance to be brought into contact with the cells varies depending on the type of the substance. For example, the concentration is about 0.001 to 100 μg/ml.

The antidiabetic drug candidate selected by the present screening method may further be subjected to a pharmacological effectiveness test or pharmacological safety test using pathological animal models, thereby producing a further useful antidiabetic drug.

EXAMPLES

The present invention is more specifically explained below with reference to Examples. However, the present invention is not limited to these examples, etc.

An EGFPS-ATF6d expression vector and an EGFPL expression vector were produced using a green fluorescent protein GFP as a reporter protein. An ATF6 activity reporter system having the two vectors was introduced into the following cell strains. As shown in FIG. 4, the EGFPS-ATF6d expression vector was produced by inserting a green fluorescent protein cDNA fragment (portion 1 (SEQ ID NO: 18) in FIG. 4: a DNA fragment encoding an amino acid region of the 216th to 231st (amino acid number) amino acids in SEQ ID NO: 1), a spacer (portion 2 (SEQ ID NO: 19) in FIG. 4: a DNA fragment encoding an amino acid sequences GGGSGGGS (SEQ ID NO: 10)), a 3XFLAG tag (portion 3 (SEQ ID NO: 20) in FIG. 4: a DNA fragment encoding an amino acid sequence DYKDHDGDYKDHDIDYKDDDDK (SEQ ID NO: 11)), a nuclear localization signal (portion 4 (SEQ ID NO: 21) in FIG. 4: a DNA fragment encoding an amino acid sequence DPKKKRKVx3 (SEQ ID NO: 12)), a PEST sequence (portion 5 (SEQ ID NO: 22) in FIG. 3: a DNA fragment encoding an amino acid sequence SHGFPPEVE-EQDDGTLPMSCAQESGMDRHPAACASARINV (SEQ ID NO: 9)), and a partial cDNA fragment of mice ATF6α (portion 6 (SEQ ID NO: 23) in FIG. 4: a DNA fragment encoding an amino acid region of the 361st to 656th amino acids in SEQ ID NO: 2) into pEGFP-Puro. As shown in FIG. 5, the EGFPL expression vector was produced by inserting a nuclear localization signal (portion 7 (SEQ ID NO: 25) in FIG. 5: a DNA fragment encoding an amino acid sequence DPKKKRKVx3 (SEQ ID NO: 12)) and a green fluorescent protein cDNA fragment (portion 8 (SEQ ID NO: 26) in FIG. 5: an amino acid region of the 1st to 215th amino acids in SEQ ID NO: 1) into pEGFP-N1. pEGFP-Puro and pEGFP-N1 are capable of high expression of genes inserted into the downstream of the cytomegalovirus promoter and the enhancer in mammal cells.

1. Production of EGFPS-ATF6d Expression Vector

The production of the EGFPS-ATF6d expression vector was performed in the following three steps.

Step 1: Through artificial gene synthesis, four types of double strand DNA individually encoding a green fluorescent protein cDNA fragment, a spacer, a 3XFLAG tag, and a nuclear localization signal (portions 1, 2, 3, and 4 in FIG. 4) were synthesized and inserted into a pEGFP-Puro expression vector, thereby producing an EGFPS expression vector.

Step 2: A mouse ATF6α partial cDNA fragment (portions 6 in FIG. 4) obtained by PCR of kpn.mATF6d.SP1 (sequence: 5'-CTAGGGTACCCCAAAGCGAAGAGCTGTCTG-3' (SEQ ID NO: 13)) and not.mATF6d.AP1 (sequence: 5'-TTTTTTCCTTGCGGCCGCCTACTGCAAC-GACTCAGGGA-3' (SEQ ID NO: 14)) from mouse cDNA was inserted into a EGFPS expression vector, thereby producing a EGFPS-ATF6d-PEST(–) expression vector.

Step 3: A mouse ODC PEST sequence (portion 5 in FIG. 4) obtained by PCR of xho.PEST.SP1 (sequence: 5'-CTAGCTCGAGAGCCATGGCTTCCCGCCGGC-3' (SEQ ID NO: 15)) and kpn.PEST.AP1 (sequence: 5'-CTAGGGTACCCACATTGATCCTAGCAGAAG-3' (SEQ ID NO: 16)) from mouse cDNA was inserted into an EGFPS-ATF6d-PEST(–) expression vector, thereby producing an EGFPS-ATF6d expression vector.

The EGFPS expression vector, the EGFPS-ATF6d-PEST(–) expression vector, and the EGFPS-ATF6d expression vector also have a pEGFP-Puro derived puromycin drug resistance gene.

2. Production of EGFPL Expression Vector

Through artificial gene synthesis, two double-strand DNA individually encoding a nuclear localization signal and a green fluorescent protein (portions 7 and 8 in FIG. 5) were synthesized and inserted into a pEGFP-N1 expression vector, thereby producing a EGFPL expression vector. The EGFPL expression vector also has a neomycin drug resistance gene.

3. Cell Culture

Unless otherwise specified, HEK293 cells (ATCC No.: CRL-1573), MIN6 cells (pancreatic β-cells reported by Miyazaki J et al., Endocrinology 127:126-132(1990)), HepG2 cells (ATCC No.: HB-8065), 3T3-L1 cells (ATCC No.: CL-173), L6 cells (ATCC No.: CRL-1458), and the cells introduced in the ATF6 activity reporter system (described later) were cultured under a condition of 37° C. and 5% $CO_2$ using a culture medium obtained by adding 10% fetal bovine serum to DMEM.

4. Preparation of Cells Containing ATF6 Activity Reporter System

The EGFPS-ATF6d expression vector and the EGFPL expression vector were introduced into HEK293 cells using a polyethylene imine method at an efficiency of not less than 90%. Through an electroporation method using NEON (electroporation device) (Invitrogen), the EGFPS-ATF6d expression vector and the EGFPL expression vector were introduced into MIN6 cells, HepG2 cells, 3T3-L1 cells, and L6 cells at an efficiency of not less than 80%, 60%, 90%, and 70%, respectively.

5. Confirmation of ATF6 Activity Reporter System

In order to confirm that the ATF6 activity reporter system functions in an endoplasmic reticulum stress-dependent manner, the EGFPS-ATF6d expression vector and the EGFPL expression vector were coexpressed or individually expressed in HEK293 cells. The fluorescence signal of the cells was observed with an inverted fluorescence microscope DMI6000B (Leica); and a fluorescence signal was captured by a Rolera-XR CCD camera (QImaging) and analyzed using "Image-Pro Plus" software (Media Cybernetics; image analysis software).

Figure 6:
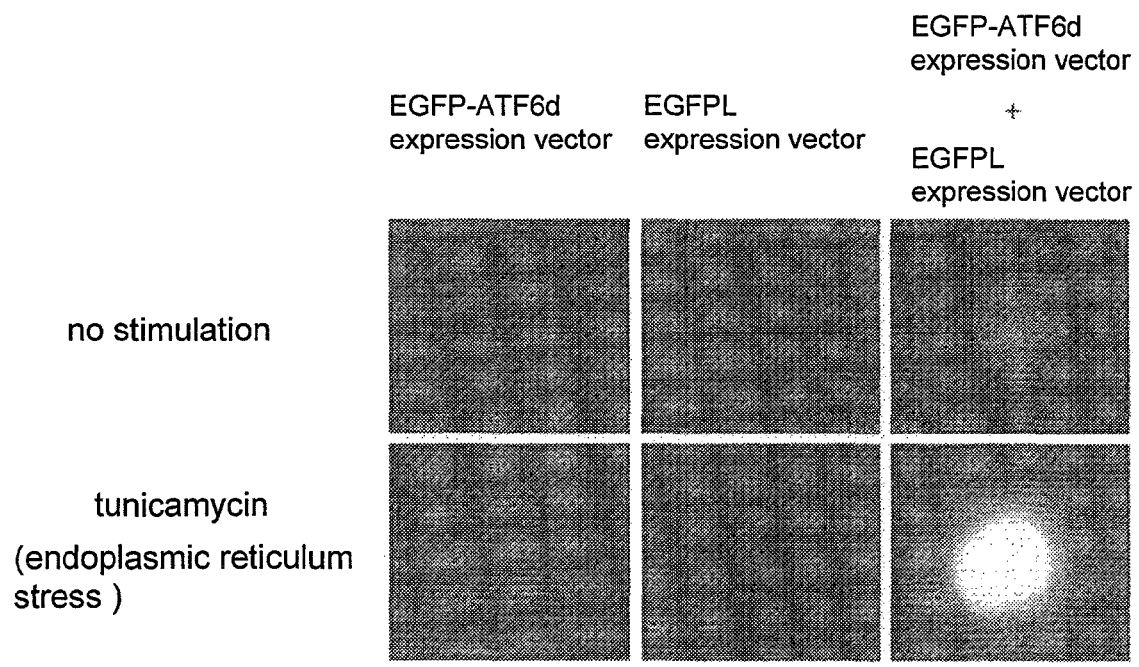
FIG. 6 shows a result of confirmation of the function of an ATF6 activity reporter system.

As shown in FIG. 6, under general culture conditions, no green fluorescence was observed in the cells in which the EGFPS-ATF6d expression vector and the EGFPL expression vector were individually expressed. In the cells in which the EGFPS-ATF6d expression vector and the EGFPL expression vector were coexpressed, green fluorescence was slightly observed. The cells were stimulated with 0.2 ug/ml tunicamycin, which is an endoplasmic reticulum stress inducer, and observed 6 hours after the stimulation. As a result, no green fluorescence was observed in the cells in which the EGFPS-ATF6d expression vector and the EGFPL expression vector were individually expressed, and significant green fluorescence was observed in the cells in which the EGFPS-ATF6d expression vector and the EGFPL expression vector were coexpressed.

This showed that the divided green fluorescent proteins do not individually yield fluorescence, and that the ATF6 activity reporter system functions in response to endoplasmic reticulum stress.

6. Confirmation of Endoplasmic Reticulum Stress Specificity of Atf6 Activity Reporter System It is important that ATF6 activity reporter system is capable of detecting ATF6 activation in an endoplasmic reticulum stress-specific manner. Therefore, HEK293 cells in which the EGFPS-ATF6d expression vector and the EGFPL expression vector are coexpressed are stimulated by etoposide, which is a DNA replication inhibitor; thapsigargin, which is an endoplasmic reticulum stress inducer; and DTT, which is an endoplasmic reticulum stress inducer, in an amount of 100 uM, 0.2 uM, and 1 mM, respectively; and the presence of fluorescence was observed. With Hoechst33258 staining, it was confirmed that the induced stresses were all severe enough to cause cell death after 36 hours.

Figure 7:
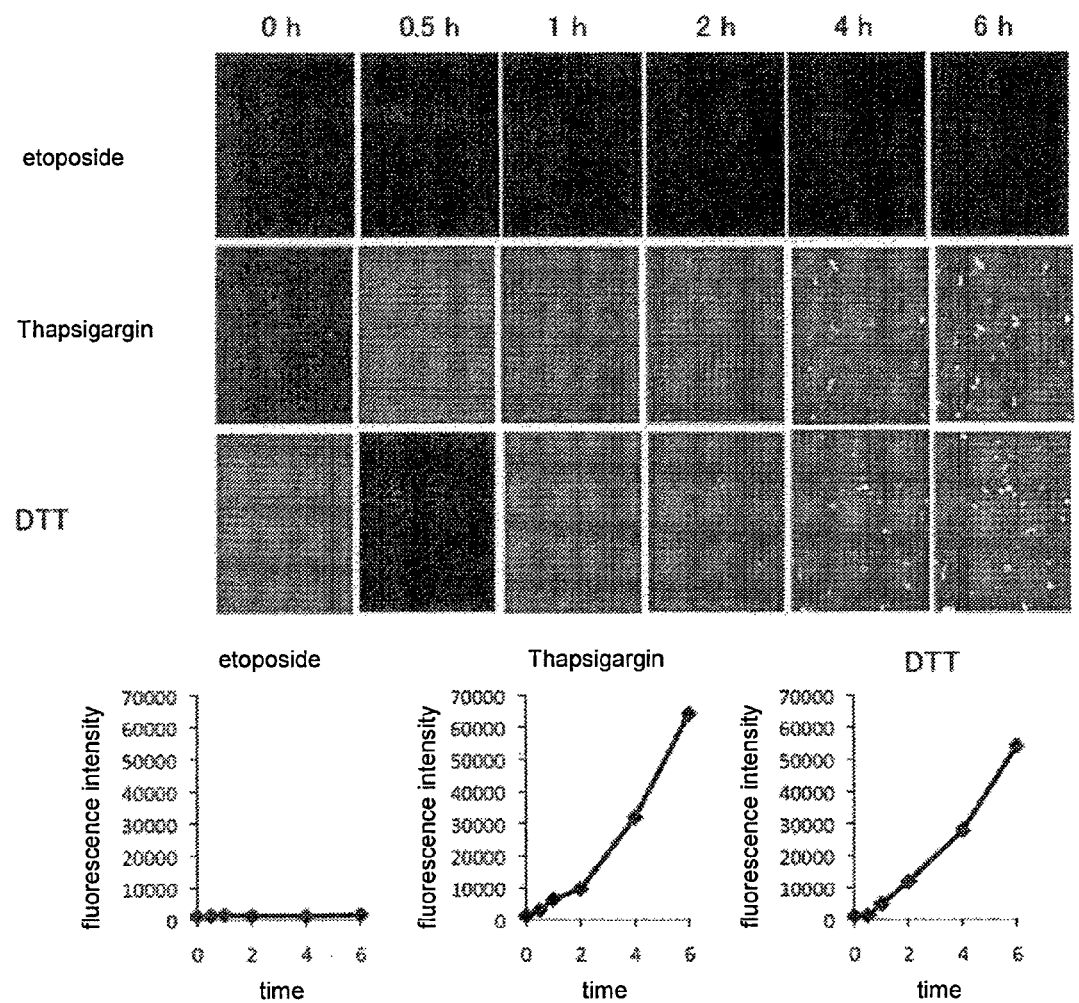
FIG. 7 shows a result of confirmation of the endoplasmic reticulum stress specificity of an ATF6 activity reporter system.

However, as shown in FIG. 7, no green fluorescence was observed in the cells stimulated by etoposide, which is irrelevant to endoplasmic reticulum stress; and significant green fluorescence was observed in the cells stimulated by thapsigargin or DTT, which are endoplasmic reticulum stress inducers.

This showed that the ATF6 activity reporter system is capable of detection of ATF6 activation in an endoplasmic reticulum stress-specific manner.

7. Confirmation of Specificity of Endoplasmic Reticulum Stress Response Pathway of ATF6 Activity Reporter System The endoplasmic reticulum stress response is known to be controlled by three individual pathways. It is important that the ATF6 activity reporter system enables detection of ATF6 activation with no influence of other pathways, such as Ire1 pathway or PERK pathway. In this connection, the EGFPS-ATF6d expression vector and the EGFPL expression vector were coexpressed in mouse fibroblasts modified by deleting Ire1α gene or PERK gene. The cells were observed 6 hours after stimulation with 0.2 ug/ml tunicamycin, which is an endoplasmic reticulum stress inducer.

Figure 8:
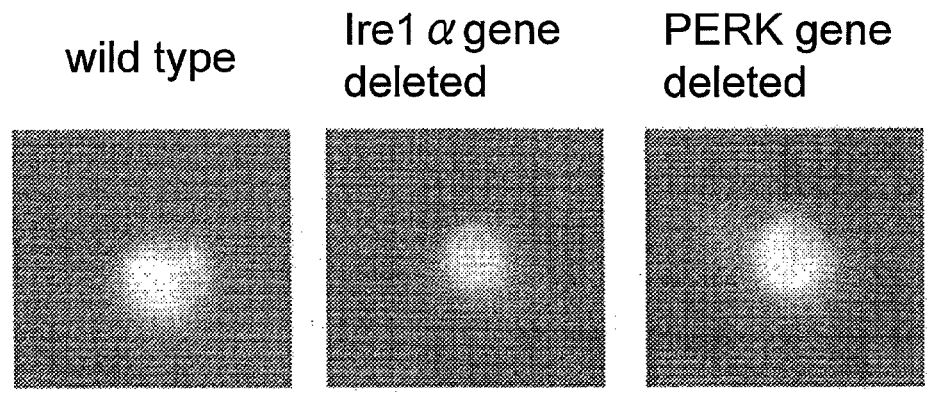
FIG. 8 shows a result of confirmation of the specificity of an endoplasmic reticulum stress response pathway of the ATF6 activity reporter system.

As shown in FIG. 8, significant green fluorescence was observed both in the fibroblast modified by Ire1α gene deletion, and in the fibroblast modified by PERK gene deletion due to the stimulation with tunicamycin.

This showed that the ATF6 activity reporter system is capable of detection of ATF6 activation with no influence of Ire1 pathway or PERK pathway.

8. Confirmation of Importance of Spacer in Egfps-Atf6d Expression Vector

To obtain a high fluorescence signal, efficient restructuring of the divided fluorescence green proteins is necessary. Thus, it is important to add an appropriate spacer that does not hinder the association of the divided fluorescence green proteins. To find an appropriate length of the spacer, as shown in FIG. 9, two double-strand DNA were produced through artificial gene synthesis, and inserted into a pEGFPS-ATF6d expression vector so as to produce a pEGFPS-ATF6d-SP1 expression vector and a pEGFPS-ATF6d-SP3 expression vector that respectively have a spacer GGGS (SEQ ID NO: 5) and a spacer GGGSGGGSGGGS (SEQ ID NO: 6). HEK293 cells in which an EGFPL expression vector and either a pEGFPS-ATF6d-SP1 expression vector (spacer GGGS (SEQ ID NO: 5)), an EGFPS-ATF6d expression vector (spacer GGGSGGGS SEQ ID NO: 10)), or a pEGFPS-ATF6d-SP3 expression vector (spacer GGGSGGGSGGGS (SEQ ID NO: 6)) were coexpressed were stimulated with 0.2 ug/ml tunicamycin, which is an endoplasmic reticulum stress inducer. Six hours after the stimulation, the cells were observed.

Figure 10:
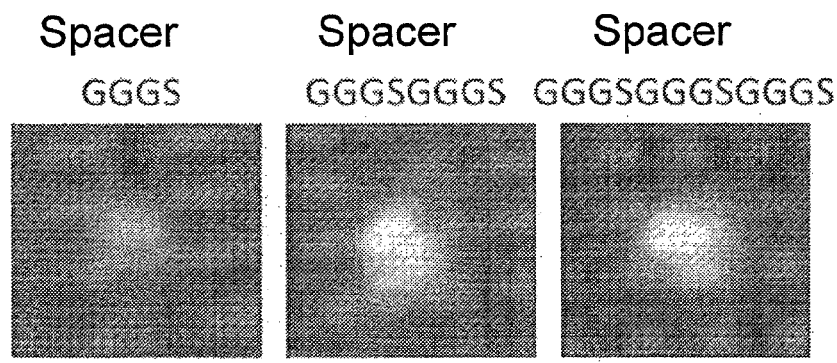
FIG. 10 shows a result of confirmation of the importance of the spacer in the EGFP-ATF6d expression vector. The results of spacer GGGS (SEQ ID NO: 5), spacer GGGSGGGS (SEQ ID NO: 10), and spacer GGGSGGGSGGGS (SEQ ID NO: 6) are shown.

As shown in FIG. 10, the green fluorescence was more significantly observed in the cells in which the spacer GGGSGGGS (SEQ ID NO: 10) or the spacer GGGSGGGSGGGSGGGS (SEQ ID NO: 6), both longer than the spacer GGGS (SEQ ID NO: 5), was expressed.

This confirmed the importance of the length of the spacer in the present system.

9. Confirmation of Importance of PEST Sequence in EGFPS-ATF6d Expression Vector

The endoplasmic reticulum stress response is indispensable for the homeostasis of endoplasmic reticulum. The endoplasmic reticulum stress response is induced not only under a pathological condition, but also under a physiological condition. In the cells cultured under a general culture condition, weak endoplasmic reticulum stress response is usually induced. Accordingly, in the cells in which the ATF6 activity reporter system is expressed, the endoplasmic reticulum stress is assumed to cause accumulation of green fluorescent protein serving as a reporter, thereby producing a high background signal. In this regard, the cells in which a EGFPL expression vector and either an EGFPS-ATF6d expression vector for expressing a mouse ODC PEST sequence that promotes degradation of green fluorescent protein, or an EGFPS-ATF6d-PEST(-) expression vector that does not have a mouse ODC PEST sequence are coexpressed were stimulated with 2 ug/ml tunicamycin, which is an endoplasmic reticulum stress inducer. The cells were observed before the stimulation, and 6 hour after the stimulation.

Figure 11:
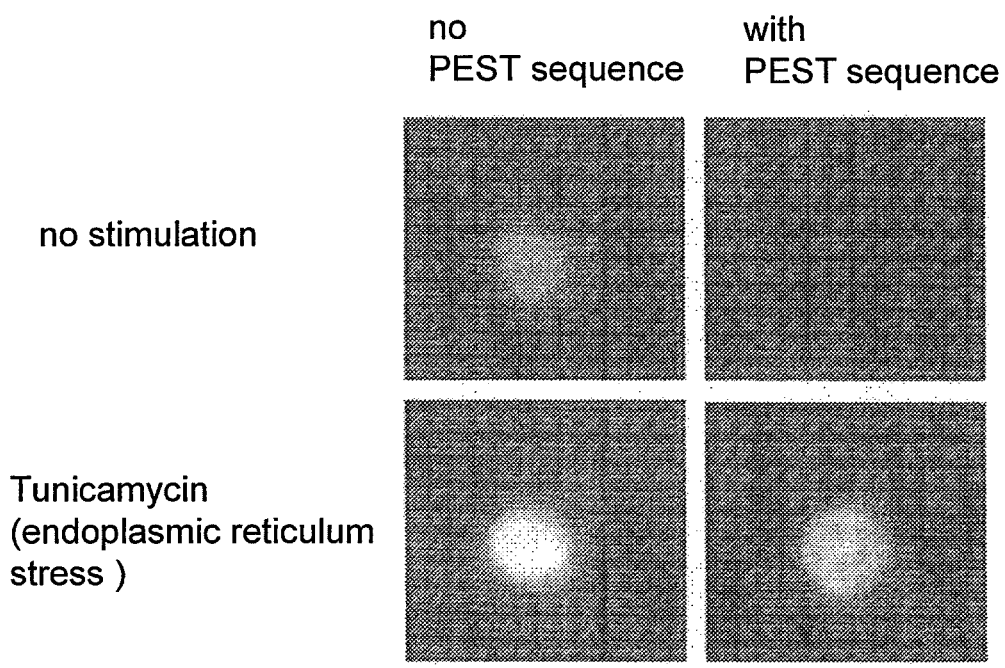
FIG. 11 shows a result of confirmation of the importance of PEST sequence in an EGFP-ATF6d expression vector.

As shown in FIG. 11, green fluorescence was significantly weakened by a PEST sequence in the cells cultured under a general culture condition. Under the stimulation with tunicamycin, although the induction of green fluorescence was slightly decreased by the PEST sequence, the rate of increase in green fluorescence luminance by the stimulation was increased by the PEST sequence.

This confirmed the importance of the PEST sequence in the present system.

Figure 12:
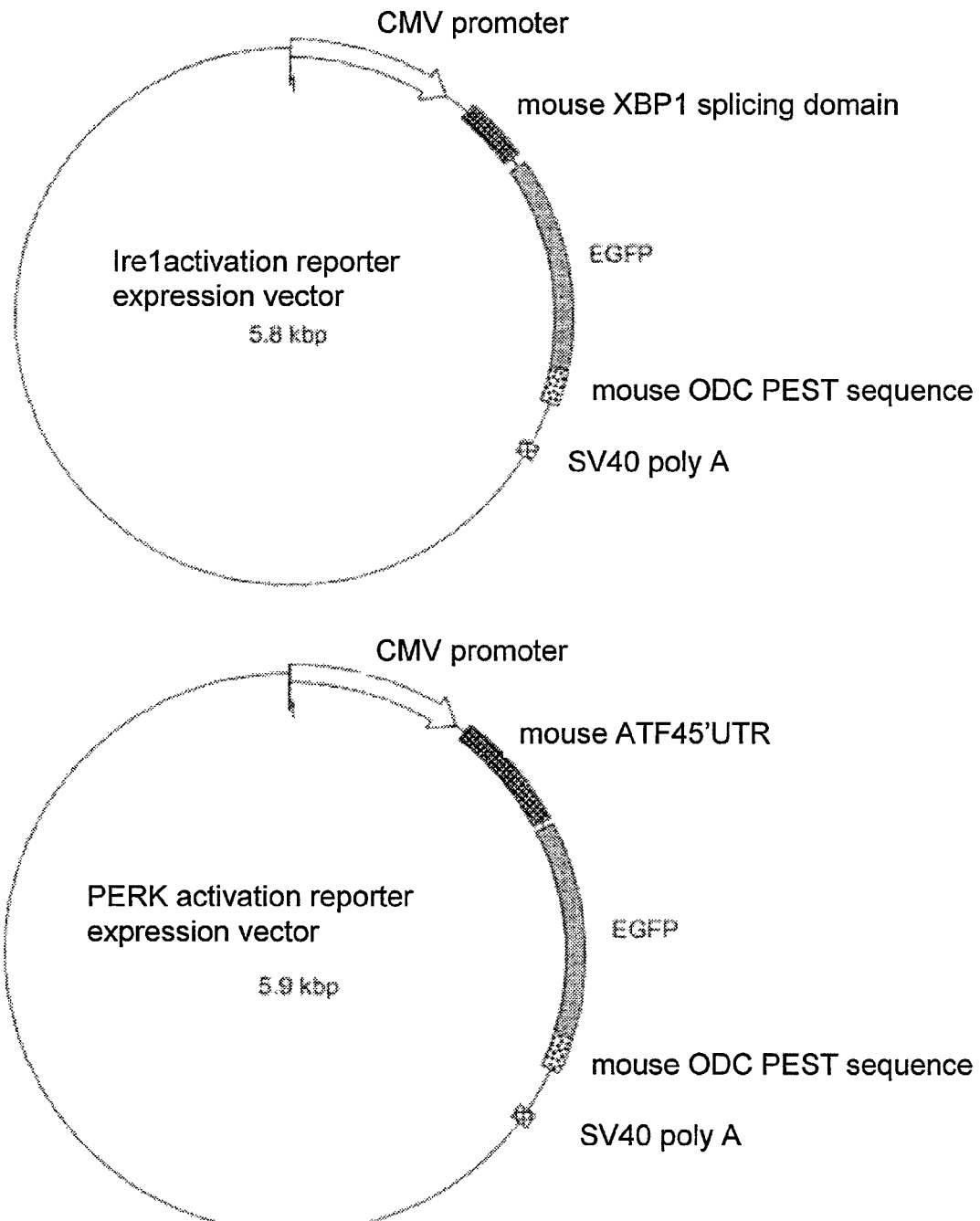
FIG. 12 shows a vector map of an Ire1 activation reporter vector for measuring Ire1 pathway by XBP splicing, and a vector map of a PERK activation reporter expression vector for measuring PERK pathway by ATF4 translation.
Figure 13:
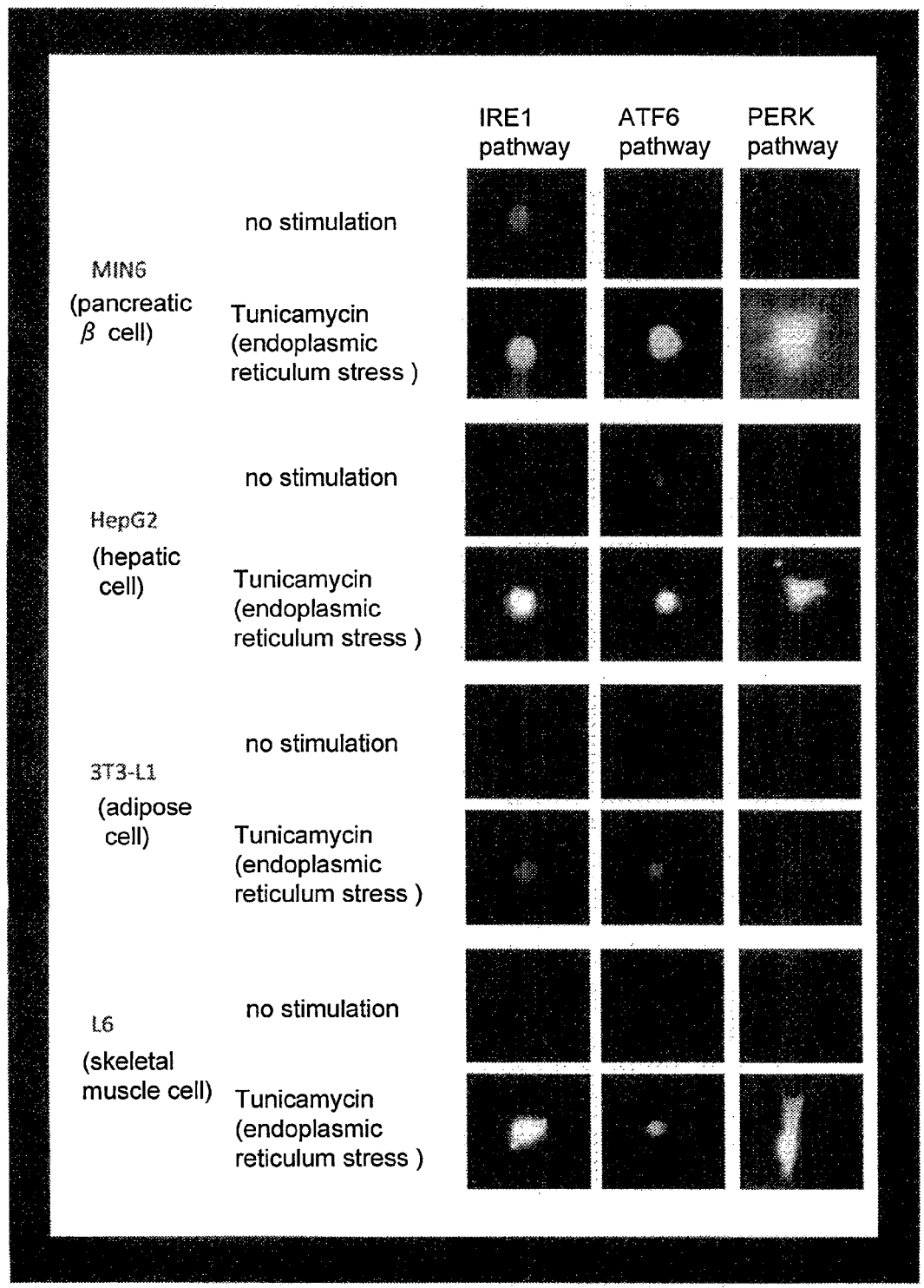
FIG. 13 shows the difference between endoplasmic reticulum stress response signals of different organs (fluorescence microscope image).

10. Confirmation of Detection of Difference in Organ-Specific Endoplasmic Reticulum Stress Response Signal Using ATF6 Activity Reporter System The endoplasmic reticulum stress response is controlled by the three pathways, namely, Ire1 pathway, PERK pathway, and ATF6 pathway. Apart from the homeostasis of endoplasmic reticulum, they are also individually involved in control of organ-specific metabolism. Detection of the three endoplasmic reticulum stress response pathways is considered important to discover a drug targeting organ-specific endoplasmic reticulum stress response with fewer side effects. In this regard, as shown in FIG. 12, an Ire1 activation reporter expression vector, disclosed in Nat. Med. (2004) 10 98-102, for measuring Ire1 pathway by XBP1 splicing, and a PERK activation reporter expression vector, disclosed in J Cell Biol. (2004) 167 27-33, for measuring PERK pathway by ATF4 translation were produced. An EGFPS-ATF6d expression vector, an EGFPL expression vector, the Ire1 activation reporter expression vector, and the PERK activation reporter expression vector were expressed in pancreatic β-cell strain MIN6 cells, hepatic cell strain HepG2 cells, adipose cell strain 3T3-L1 cells, and skeletal muscle cell strain L6 cells, respectively. The cells were observed 6 hours after the stimulation with 0.2 ug/ml tunicamycin, which is an endoplasmic reticulum stress inducer. FIG. 13 shows an image of fluorescence in the cells observed with an inverted fluorescence microscope DMI6000B (Leica). Further, FIG. 14 shows the results of determination of fluorescence intensity of the cells measured by "Image-Pro Plus" (Media Cybernetics) software using a fluorescence microscope cell image captured by a CCD camera Rolera-XR (QImaging).

As shown in FIG. 13, the endoplasmic reticulum stress response signal varies in each cell group derived from a different organ, even under the same stress conditions.

Figure 14:
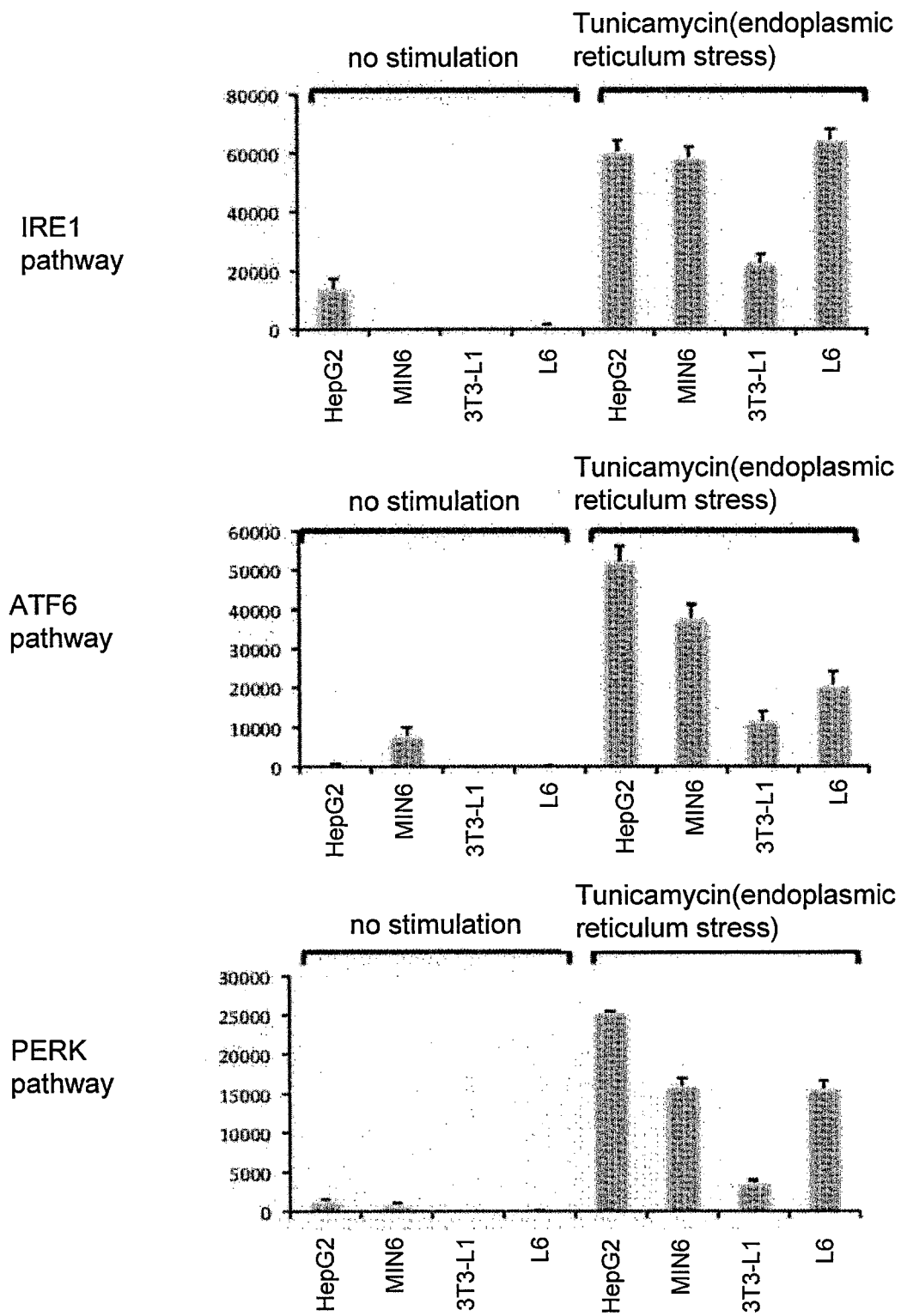
FIG. 14 shows the difference between endoplasmic reticulum stress response signals of different organs (measurement results of fluorescence intensity).

Further, as shown in FIG. 14, the activation of IRE1 pathway by tunicamycin is relatively high in hepatic cell strain HepG2 cells, pancreatic β-cell strain MIN6 cells and skeletal muscle cell strain L6 cells, and relatively low in adipose cell strain 3T3-L1 cells. Further, the intensity of activation of ATF6 pathway by tunicamycin is highest in hepatic cell strain HepG2 cells, followed by pancreatic β-cell strain MIN6 cells, skeletal muscle cell strain L6 cells, and adipose cell strain 3T3-L1 cells in descending order. Further, the degree of the activation of PERK pathway by tunicamycin is highest in hepatic cell strain HepG2 cells (pancreatic β-cell strain MIN6 cells and skeletal muscle cell strain L6 cells), followed by adipose cell strain 3T3-L1 cells.

This showed that the combination of the present system with a hitherto-known technique enables confirmation of the organ-specific difference in signal intensity from the three endoplasmic reticulum stress response pathways. Further, it was also confirmed that it is possible to screen an endoplasmic reticulum stressor that activates only the ATF6 pathway among three pathways (pathways mediated by IRE1α, PERK, and ATF6), or an endoplasmic reticulum stressor that activates at least one pathway selected from the group consisting of the ATF6 pathway, IRE1α pathway, and PERK pathway.

11. Inhibition of Insulin Secretion in Pancreatic β-Cells

Figure 15:
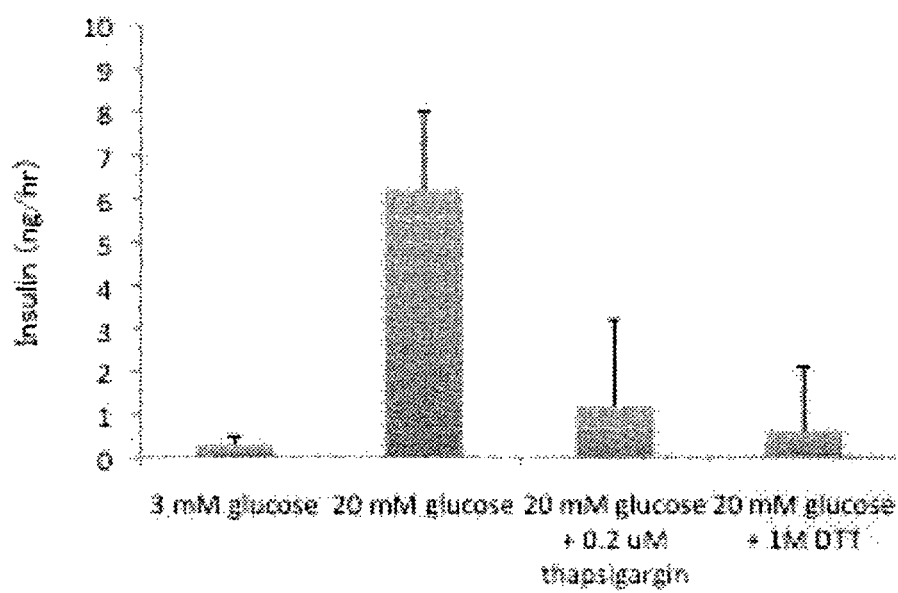
FIG. 15 shows inhibition of insulin secretion in pancreatic β-cells by an insulin endoplasmic reticulum stressor.

A control solution (DMSO), a thapsigargin solution (thapsigargin/DMSO solution), or a DTT solution (DTT/DMSO solution) was added to a culture solution (DMEM containing 10% fetal bovine serum) in which pancreatic p-cell MIN6 cells are cultured, and the culture solution was replaced with a general culture solution (DMEM containing 10% fetal bovine serum) after 30 minutes. Then, the culture was continued for 36 hours. The thapsigargin solution was added so that the thapsigargin concentration in the culture solution became 0.2 uM, and the DTT solution was added so that the DTT concentration in the culture solution became 1 M. Thereafter, the culture solution was replaced with a KREBS buffer solution containing 3 mM or 20 mM glucose, and the culture was continued for 1 hours. The concentration of insulin secreted in the culture solution was measured according to the ELISA method. FIG. 15 shows the results.

As shown in FIG. 15, by the addition of thapsigargin or DTT, which is an endoplasmic reticulum stress inducer, insulin secretion was suppressed.

12. Comparison of Detection Sensitivity Between ATF6 Activity Reporter System and Hitherto-Known Method (Western Blotting)

A comparison of detection sensitivity in the detection of ATF6 pathway activation between the ATF6 activity reporter system and a hitherto-known method (western blotting) was conducted.

The detection sensitivity of the ATF6 activity reporter system was measured as follows. Adipose cell strain 3T3-L1 cells obtained in the same manner as in "4. Preparation of Cells containing ATF6 Activity Reporter System" were stimulated using a known differentiation-inducing stimulation method (exposure to insulin, dexamethasone, and 3-isobutyl-1-methylxanthine). 14 days after the stimulation, a test compound (one of Compounds 1 to 10) was added as an endoplasmic reticulum stressor candidate substance, and a stimulator (palmitic acid) for inducing endoplasmic reticulum stress or the like was added after 6 hours so that the final concentration became 400 μM. After another 16 hours, the cell image was obtained by an inverted fluorescence microscope DMI6000B (Leica), and the intensity of fluorescence emitted from the cells was measured using "Image-Pro Plus" (Media Cybernetics) image analysis software.

The detection sensitivity in the hitherto-known method (western blotting) was measured as follows. Adipose cell strain 3T3-L1 cells were stimulated using a known differentiation-inducing stimulation method (exposure to insulin, dexamethasone, and 3-isobutyl-1-methylxanthine). 14 days after the stimulation, a test compound (one of Compounds 1 to 10) was added, and a stimulator for inducing endoplasmic reticulum stress or the like was added after 6 hours. After another 16 hours, the cells were collected. A cell extract was prepared from the obtained cells, and the expression amount of ATF6α protein was detected through western blotting using anti-ATF6 alfa antibody mouse monoclonal (BioAcademia 73-505). The detected signal intensity was measured using "Image-Pro Plus" (Media Cybernetics) software.

Figure 16:
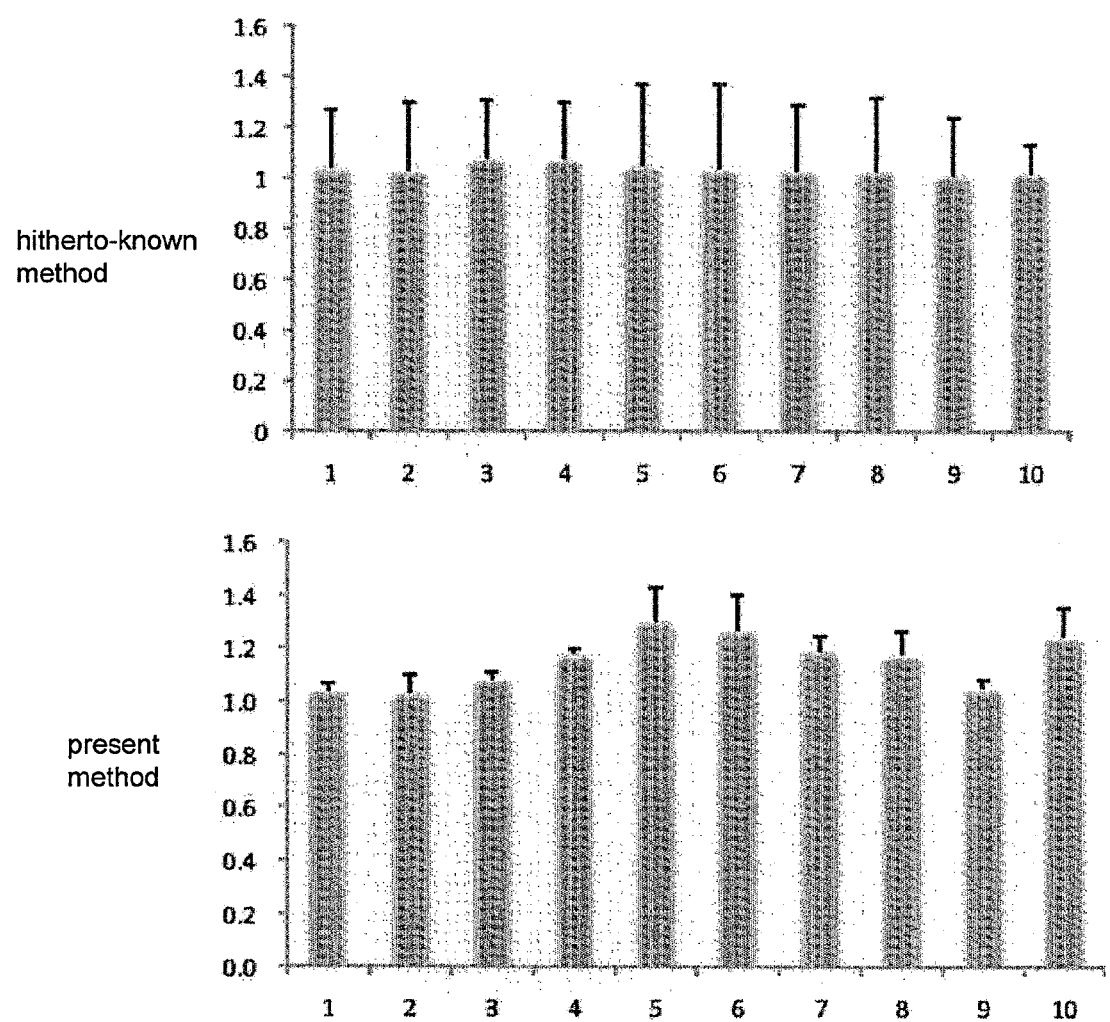
FIG. 16 shows a sensitivity during the detection of ATF6 pathway activation using a ATF6 activity reporter system, which is superior to the sensitivity during the detection using a hitherto-known method (western blotting).

FIG. 16 shows the results. The fluorescence intensity or signal intensity in the vertical axis is denoted by a value that is determined by assuming that the intensity in the control (test compound is not added) is 1. More specifically, 1 or more intensity in the vertical axis indicates activation of ATF6 pathway by the test compound. The horizontal axis shows the numbers (1-10) of the test compounds.

Activation of ATF6 pathway was not observed by the addition of any of the test compounds 1 to 10 in the hitherto-known method. In contrast, in the present method, activation of ATF6 pathway was observed when the test compounds 4, 5, 6, 7, 8, or 10 was added (1.2 times the control).

The results showed that the present method is capable of detecting a very small amount of activation of ATF6 pathway, which is not detectable by the hitherto-known method. More specifically, the present method ensures a detection sensitivity significantly superior to the detection sensitivity of the hitherto-known method. [Sequence Table]

SEQUENCE LISTING

<160> NUMBER OF SEQ ID NOS: 28

<210> SEQ ID NO 1
<211> LENGTH: 231
<212> TYPE: PRT
<213> ORGANISM: Artificial
<220> FEATURE:
<223> OTHER INFORMATION: EGFP amino acid sequence

<400> SEQUENCE: 1

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Ile Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Tyr Gly Val Gln Cys Phe Ser Arg Tyr Pro Asp His Met Lys
65                  70                  75                  80

Arg His Asp Phe Phe Lys Ser Ala Met Pro Glu Gly Tyr Val Gln Glu
                85                  90                  95

Arg Thr Ile Ser Phe Lys Asp Asp Gly Lys Tyr Lys Thr Arg Ala Val
                100                 105                 110

Val Lys Phe Glu Gly Asp Thr Leu Val Asn Arg Ile Glu Leu Lys Gly
            115                 120                 125

Thr Asp Phe Lys Glu Asp Gly Asn Ile Leu Gly His Lys Leu Glu Tyr
    130                 135                 140

Asn Phe Asn Ser His Asn Val Tyr Ile Thr Ala Asp Lys Gln Lys Asn
145                 150                 155                 160

Gly Ile Lys Ala Asn Phe Thr Val Arg His Asn Val Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Thr Val Leu
    195                 200                 205

Ser Lys Asp Pro Asn Glu Lys Arg Asp His Met Val Leu His Glu Tyr
210                 215                 220

Val Asn Ala Ala Gly Ile Thr
225                 230

<210> SEQ ID NO 2
<211> LENGTH: 656
<212> TYPE: PRT
<213> ORGANISM: Mus musculus

<400> SEQUENCE: 2

Met Glu Ser Pro Phe Ser Pro Val Leu Pro His Gly Pro Asp Glu Asp
1               5                   10                  15

Trp Glu Ser Thr Leu Phe Ala Glu Leu Gly Tyr Phe Thr Asp Thr Asp
                20                  25                  30

Asp Val His Phe Asp Ala Ala His Glu Ala Tyr Glu Asn Asn Phe Asp
            35                  40                  45

His Leu Asn Phe Asp Leu Asp Leu Met Pro Trp Glu Ser Asp Leu Trp
    50                  55                  60

Ser Pro Gly Ser His Phe Cys Ser Asp Met Lys Ala Glu Pro Gln Pro
65                  70                  75                  80

Leu Ser Pro Ala Ser Ser Ser Cys Ser Ile Ser Ser Pro Arg Ser Thr
                85                  90                  95

Asp Ser Cys Ser Ser Thr Gln His Val Pro Glu Glu Leu Asp Leu Leu
            100                 105                 110

Ser Ser Ser Gln Ser Pro Leu Ser Leu Tyr Gly Asp Ser Cys Asn Ser
    115                 120                 125

Pro Ser Ser Val Glu Pro Leu Lys Glu Glu Lys Pro Val Thr Gly Pro
130                 135                 140

Gly Asn Lys Thr Glu His Gly Leu Thr Pro Lys Lys Lys Ile Gln Met
145                 150                 155                 160

Ser Ser Lys Pro Ser Val Gln Pro Lys Pro Leu Leu Leu Pro Ala Ala
                165                 170                 175

Pro Lys Thr Gln Thr Asn Ala Ser Val Pro Ala Lys Ala Ile Ile Ile
            180                 185                 190

```
Gln Thr Leu Pro Ala Leu Met Pro Leu Ala Lys Gln Gln Ser Ile Ile
            195                 200                 205

Ser Ile Gln Pro Ala Pro Thr Lys Gly Gln Thr Val Leu Leu Ser Gln
        210                 215                 220

Pro Thr Val Val Gln Leu Gln Ser Pro Ala Val Leu Ser Ser Ala Gln
225                 230                 235                 240

Pro Val Leu Ala Val Thr Gly Gly Ala Ala Gln Leu Pro Asn His Val
                245                 250                 255

Val Asn Val Leu Pro Ala Pro Val Val Ser Ser Pro Val Asn Gly Lys
                260                 265                 270

Leu Ser Val Thr Lys Pro Val Leu Gln Ser Ala Thr Arg Ser Met Gly
            275                 280                 285

Ser Asp Ile Ala Val Leu Arg Arg Gln Gln Arg Met Ile Lys Asn Arg
290                 295                 300

Glu Ser Ala Cys Gln Ser Arg Lys Lys Lys Glu Tyr Met Leu Gly
305                 310                 315                 320

Leu Glu Ala Arg Leu Lys Ala Ala Leu Ser Glu Asn Glu Gln Leu Lys
                325                 330                 335

Lys Glu Asn Gly Ser Leu Lys Arg Gln Leu Asp Glu Val Val Ser Glu
            340                 345                 350

Asn Gln Arg Leu Lys Val Pro Ser Pro Lys Arg Arg Ala Val Cys Val
            355                 360                 365

Met Ile Val Leu Ala Phe Ile Met Leu Asn Tyr Gly Pro Met Ser Met
370                 375                 380

Leu Glu Gln Glu Ser Arg Arg Val Lys Pro Ser Val Ser Pro Ala Asn
385                 390                 395                 400

Gln Arg Arg His Leu Leu Glu Phe Ser Ala Lys Glu Val Lys Asp Thr
                405                 410                 415

Ser Asp Gly Asp Asn Gln Lys Asp Ser Tyr Ser Tyr Asp His Ser Val
            420                 425                 430

Ser Asn Asp Lys Ala Leu Met Val Leu Ser Glu Glu Pro Leu Leu Tyr
            435                 440                 445

Met Pro Pro Pro Cys Gln Pro Leu Ile Asn Thr Thr Glu Ser Leu
            450                 455                 460

Arg Leu Asn His Glu Leu Arg Gly Trp Val His Arg His Glu Val Glu
465                 470                 475                 480

Arg Thr Lys Ser Arg Met Thr Asn Ser Gln Lys Ala Arg Ile
                485                 490                 495

Leu Gln Gly Ala Leu Glu Gln Gly Ser Asn Ser Gln Leu Met Ala Val
            500                 505                 510

Gln Tyr Thr Glu Thr Ser Ile Ser Arg Asn Ser Gly Ser Glu Leu
            515                 520                 525

Gln Val Tyr Tyr Ala Ser Pro Gly Ser Tyr Gln Gly Phe Phe Asp Ala
            530                 535                 540

Ile Arg Arg Arg Gly Asp Thr Phe Tyr Val Val Ser Phe Arg Arg Asp
545                 550                 555                 560

His Leu Leu Leu Pro Ala Thr His Asn Lys Thr Thr Arg Pro Lys
                565                 570                 575

Met Ser Ile Val Leu Pro Ala Ile Asn Ile Asn Asp Asn Val Ile Asn
            580                 585                 590

Gly Gln Asp Tyr Glu Val Met Met Gln Ile Asp Cys Gln Val Met Asp
            595                 600                 605
```

```
Thr Arg Ile Leu His Ile Lys Ser Ser Val Pro Pro Tyr Leu Arg
    610                 615                 620

Asp His Gln Arg Asn Gln Thr Ser Thr Phe Phe Gly Ser Pro Pro Thr
625                 630                 635                 640

Thr Thr Glu Thr Thr His Val Val Ser Thr Ile Pro Glu Ser Leu Gln
                645                 650                 655

<210> SEQ ID NO 3
<211> LENGTH: 670
<212> TYPE: PRT
<213> ORGANISM: Homo sapiens

<400> SEQUENCE: 3

Met Gly Glu Pro Ala Gly Val Ala Gly Thr Met Glu Ser Pro Phe Ser
1               5                   10                  15

Pro Gly Leu Phe His Arg Leu Asp Glu Asp Trp Asp Ser Ala Leu Phe
            20                  25                  30

Ala Glu Leu Gly Tyr Phe Thr Asp Thr Asp Glu Leu Gln Leu Glu Ala
        35                  40                  45

Ala Asn Glu Thr Tyr Glu Asn Asn Phe Asp Asn Leu Asp Phe Asp Leu
    50                  55                  60

Asp Leu Met Pro Trp Glu Ser Asp Ile Trp Asp Ile Asn Asn Gln Ile
65                  70                  75                  80

Cys Thr Val Lys Asp Ile Lys Ala Glu Pro Gln Pro Leu Ser Pro Ala
                85                  90                  95

Ser Ser Ser Tyr Ser Val Ser Ser Pro Arg Ser Val Asp Ser Tyr Ser
            100                 105                 110

Ser Thr Gln His Val Pro Glu Glu Leu Asp Leu Ser Ser Ser Ser Gln
        115                 120                 125

Met Ser Pro Leu Ser Leu Tyr Gly Glu Asn Ser Asn Ser Leu Ser Ser
    130                 135                 140

Ala Glu Pro Leu Lys Glu Asp Lys Pro Val Thr Gly Pro Arg Asn Lys
145                 150                 155                 160

Thr Glu Asn Gly Leu Thr Pro Lys Lys Lys Ile Gln Val Asn Ser Lys
                165                 170                 175

Pro Ser Ile Gln Pro Lys Pro Leu Leu Leu Pro Ala Ala Pro Lys Thr
            180                 185                 190

Gln Thr Asn Ser Ser Val Pro Ala Lys Thr Ile Ile Gln Thr Val
        195                 200                 205

Pro Thr Leu Met Pro Leu Ala Lys Gln Gln Pro Ile Ile Ser Leu Gln
210                 215                 220

Pro Ala Pro Thr Lys Gly Gln Thr Val Leu Leu Ser Gln Pro Thr Val
225                 230                 235                 240

Val Gln Leu Gln Ala Pro Gly Val Leu Pro Ser Ala Gln Pro Val Leu
                245                 250                 255

Ala Val Ala Gly Gly Val Thr Gln Leu Pro Asn His Val Val Asn Val
            260                 265                 270

Val Pro Ala Pro Ser Ala Asn Ser Pro Val Asn Gly Lys Leu Ser Val
        275                 280                 285

Thr Lys Pro Val Leu Gln Ser Thr Met Arg Asn Val Gly Ser Asp Ile
    290                 295                 300

Ala Val Leu Arg Arg Gln Gln Arg Met Ile Lys Asn Arg Glu Ser Ala
305                 310                 315                 320

Cys Gln Ser Arg Lys Lys Lys Lys Glu Tyr Met Leu Gly Leu Glu Ala
                325                 330                 335
```

```
Arg Leu Lys Ala Ala Leu Ser Glu Asn Glu Gln Leu Lys Lys Glu Asn
            340                 345                 350

Gly Thr Leu Lys Arg Gln Leu Asp Glu Val Val Ser Glu Asn Gln Arg
        355                 360                 365

Leu Lys Val Pro Ser Pro Lys Arg Val Val Cys Val Met Ile Val
    370                 375                 380

Leu Ala Phe Ile Ile Leu Asn Tyr Gly Pro Met Ser Met Leu Glu Gln
385                 390                 395                 400

Asp Ser Arg Arg Met Asn Pro Ser Val Ser Pro Ala Asn Gln Arg Arg
            405                 410                 415

His Leu Leu Gly Phe Ser Ala Lys Glu Ala Gln Asp Thr Ser Asp Gly
            420                 425                 430

Ile Ile Gln Lys Asn Ser Tyr Arg Tyr Asp His Ser Val Ser Asn Asp
            435                 440                 445

Lys Ala Leu Met Val Leu Thr Glu Glu Pro Leu Leu Tyr Ile Pro Pro
    450                 455                 460

Pro Pro Cys Gln Pro Leu Ile Asn Thr Thr Glu Ser Leu Arg Leu Asn
465                 470                 475                 480

His Glu Leu Arg Gly Trp Val His Arg His Glu Val Glu Arg Thr Lys
            485                 490                 495

Ser Arg Arg Met Thr Asn Asn Gln Gln Lys Thr Arg Ile Leu Gln Gly
            500                 505                 510

Ala Leu Glu Gln Gly Ser Asn Ser Gln Leu Met Ala Val Gln Tyr Thr
            515                 520                 525

Glu Thr Thr Ser Ser Ile Ser Arg Asn Ser Gly Ser Glu Leu Gln Val
    530                 535                 540

Tyr Tyr Ala Ser Pro Arg Ser Tyr Gln Asp Phe Phe Glu Ala Ile Arg
545                 550                 555                 560

Arg Arg Gly Asp Thr Phe Tyr Val Val Ser Phe Arg Arg Asp His Leu
            565                 570                 575

Leu Leu Pro Ala Thr Thr His Asn Lys Thr Thr Arg Pro Lys Met Ser
            580                 585                 590

Ile Val Leu Pro Ala Ile Asn Ile Asn Glu Asn Val Ile Asn Gly Gln
    595                 600                 605

Asp Tyr Glu Val Met Met Gln Ile Asp Cys Gln Val Met Asp Thr Arg
    610                 615                 620

Ile Leu His Ile Lys Ser Ser Val Pro Pro Tyr Leu Arg Asp Gln
625                 630                 635                 640

Gln Arg Asn Gln Thr Asn Thr Phe Phe Gly Ser Pro Ala Ala Thr
            645                 650                 655

Glu Ala Thr His Val Val Ser Thr Ile Pro Glu Ser Leu Gln
            660                 665                 670

<210> SEQ ID NO 4
<211> LENGTH: 238
<212> TYPE: PRT
<213> ORGANISM: Aequorea victoria

<400> SEQUENCE: 4

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45
```

Thr Thr Gly Lys Leu Pro Val Pro Trp Pro Thr Leu Val Thr Thr Phe
        50                  55                  60

Ala Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Val Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 5
<211> LENGTH: 4
<212> TYPE: PRT
<213> ORGANISM: Artificial Sequence
<220> FEATURE:
<223> OTHER INFORMATION: spacer

<400> SEQUENCE: 5

Gly Gly Gly Ser
1

<210> SEQ ID NO 6
<211> LENGTH: 12
<212> TYPE: PRT
<213> ORGANISM: Artificial Sequence
<220> FEATURE:
<223> OTHER INFORMATION: spacer

<400> SEQUENCE: 6

Gly Gly Gly Ser Gly Gly Gly Ser Gly Gly Gly Ser
1               5                   10

<210> SEQ ID NO 7
<211> LENGTH: 6
<212> TYPE: PRT
<213> ORGANISM: Artificial Sequence
<220> FEATURE:
<223> OTHER INFORMATION: the nuclear localization signal in the ATF6
      protein

<400> SEQUENCE: 7

Arg Lys Lys Lys Lys Glu
1               5

```
<210> SEQ ID NO 8
<211> LENGTH: 8
<212> TYPE: PRT
<213> ORGANISM: Artificial Sequence
<220> FEATURE:
<223> OTHER INFORMATION: the exogenous nuclear localization signal

<400> SEQUENCE: 8

Asp Pro Lys Lys Lys Arg Lys Val
1               5

<210> SEQ ID NO 9
<211> LENGTH: 40
<212> TYPE: PRT
<213> ORGANISM: Artificial Sequence
<220> FEATURE:
<223> OTHER INFORMATION: PEST sequences

<400> SEQUENCE: 9

Ser His Gly Phe Pro Pro Glu Val Glu Glu Gln Asp Asp Gly Thr Leu
1               5                   10                  15

Pro Met Ser Cys Ala Gln Glu Ser Gly Met Asp Arg His Pro Ala Ala
            20                  25                  30

Cys Ala Ser Ala Arg Ile Asn Val
        35                  40

<210> SEQ ID NO 10
<211> LENGTH: 8
<212> TYPE: PRT
<213> ORGANISM: Artificial Sequence
<220> FEATURE:
<223> OTHER INFORMATION: spacer

<400> SEQUENCE: 10

Gly Gly Gly Ser Gly Gly Gly Ser
1               5

<210> SEQ ID NO 11
<211> LENGTH: 22
<212> TYPE: PRT
<213> ORGANISM: Artificial Sequence
<220> FEATURE:
<223> OTHER INFORMATION: 3XFLAG tag

<400> SEQUENCE: 11

Asp Tyr Lys Asp His Asp Gly Asp Tyr Lys Asp His Asp Ile Asp Tyr
1               5                   10                  15

Lys Asp Asp Asp Asp Lys
            20

<210> SEQ ID NO 12
<211> LENGTH: 24
<212> TYPE: PRT
<213> ORGANISM: Artificial Sequence
<220> FEATURE:
<223> OTHER INFORMATION: nuclear localization signal

<400> SEQUENCE: 12

Asp Pro Lys Lys Lys Arg Lys Val Asp Pro Lys Lys Lys Arg Lys Val
1               5                   10                  15

Asp Pro Lys Lys Lys Arg Lys Val
            20
```

```
<210> SEQ ID NO 13
<211> LENGTH: 30
<212> TYPE: DNA
<213> ORGANISM: Artificial Sequence
<220> FEATURE:
<223> OTHER INFORMATION: primer (kpn.mATF6d.SP1)

<400> SEQUENCE: 13
ctagggtacc ccaaagcgaa gagctgtctg                                          30

<210> SEQ ID NO 14
<211> LENGTH: 38
<212> TYPE: DNA
<213> ORGANISM: Artificial Sequence
<220> FEATURE:
<223> OTHER INFORMATION: primer (not.mATF6d.AP1)

<400> SEQUENCE: 14 tttttttcctt gcggccgcct actgcaacga ctcaggga                                38

<210> SEQ ID NO 15
<211> LENGTH: 30
<212> TYPE: DNA
<213> ORGANISM: Artificial Sequence
<220> FEATURE:
<223> OTHER INFORMATION: primer (xho.PEST.SP1)

<400> SEQUENCE: 15
ctagctcgag agccatggct cccgccggc                                           30

<210> SEQ ID NO 16
<211> LENGTH: 30
<212> TYPE: DNA
<213> ORGANISM: Artificial Sequence
<220> FEATURE:
<223> OTHER INFORMATION: primer (kpn.PEST.AP1)

<400> SEQUENCE: 16
ctagggtacc cacattgatc ctagcagaag                                          30

<210> SEQ ID NO 17
<211> LENGTH: 1268
<212> TYPE: DNA
<213> ORGANISM: Artificial Sequence
<220> FEATURE:
<223> OTHER INFORMATION: DNA sequence inserted in an EGFP-ATF6d
      expression vector

<400> SEQUENCE: 17
ctagccacca tgcgtgacca catggtcctt catgagtacg taaatgctgc tgggattaca        60
ggaggaggat ccggaggtgg cagcgactac aaagaccatg acggtgatta taaagatcat       120
gacatcgact acaaggatga cgatgacaag gatccaaaaa agaagagaaa ggtagatcca       180 aaaagaaga gaaaggtaga tccaaaaaag aagagaaagg tactagcgct accggactca       240
gatctcgaga gccatggctt cccgccggcg gtggcggcgc aggatgatgg cacgctgccc       300
atgtcttgtg cccaggagag cgggatggac cgtcaccctg cagcctgtgc ttctgctagg       360
atcaatgtgg gtaccccaaa agcgaagagc tgtctgtgtga tgatagtatt agcatttata       420
atgctgaact atgggcccat gagcatgctg agcaagaat cccgaagagt gaaacctagt        480
gtgagccctg ccaatcagag gaggcatctc ttggaatttt cagcaaaaga agttaaagac       540
acatcagatg tgtgacaacca gaaagacagt tacagctatg atcactctgt gtccaatgac       600
aaagctttaa tggtgctaag tgaagagcca ttgctttata tgcctccacc tccatgtcaa       660
```

```
ccctgatta acacaacaga gtctctcagg ttgaaccatg aacttcgagg ctgggttcat      720
agacatgaag tggaaaggac caaatctaga gaatgacaa atagccaaca gaaagcccgc      780
attctccagg gtgctctgga acagggctct aattctcagc tgatggctgt ccagtacaca    840
gaaaccacta gcatcagtag gaattctggg agtgagctgc aagtgtatta cgcctcccct    900
ggaagttacc aaggcttctt tgacgccatc cgcaggaggg gagatacgtt ttacgttgtc    960
tcatttcgaa gggatcatct gctattacca gctaccaccc acaacaagac cacaagacca   1020
aaaatgtcaa ttgtattacc agcaataaac ataaatgata atgtgatcaa tgggcaggac   1080
tatgaagtaa tgatgcagat tgactgtcag gtgatggaca ccaggatcct ccacatcaaa   1140
agctcctcgg ttccccctta tctccgggat catcagcgga accaaaccag caccttcttt   1200
ggttcccctc caacaaccac agagacgacc catgtggtca gcaccatccc tgagtcgttg   1260
cagtaggc                                                            1268
```

```
<210> SEQ ID NO 18
<211> LENGTH: 51
<212> TYPE: DNA
<213> ORGANISM: Artificial Sequence
<220> FEATURE:
<223> OTHER INFORMATION: portion 1 in Fig. 4: a DNA fragment encoding an
      amino acid region of the 216th to 231st (amino acid number) amino
      acids in SEQ ID NO: 1

<400> SEQUENCE: 18
atgcgtgacc acatggtcct tcatgagtac gtaaatgctg ctgggattac a            51

<210> SEQ ID NO 19
<211> LENGTH: 24
<212> TYPE: DNA
<213> ORGANISM: Artificial Sequence
<220> FEATURE:
<223> OTHER INFORMATION: portion 2 in Fig. 4: a DNA fragment encoding
      spacer

<400> SEQUENCE: 19
ggaggaggat ccggaggtgg cagc                                           24

<210> SEQ ID NO 20
<211> LENGTH: 66
<212> TYPE: DNA
<213> ORGANISM: Artificial Sequence
<220> FEATURE:
<223> OTHER INFORMATION: portion 3 in Fig. 4: a DNA fragment encoding
      FLAG tag

<400> SEQUENCE: 20
gactacaaag accatgacgg tgattataaa gatcatgaca tcgactacaa ggatgacgat   60
gacaag                                                              66

<210> SEQ ID NO 21
<211> LENGTH: 72
<212> TYPE: DNA
<213> ORGANISM: Artificial Sequence
<220> FEATURE:
<223> OTHER INFORMATION: portion 4 in Fig. 4: a DNA fragment encoding a
      nuclear localization signal

<400> SEQUENCE: 21
gatccaaaaa agaagagaaa ggtagatcca aaaaagaaga gaaaggtaga tccaaaaaag   60
aagagaaagg ta                                                       72
```

<210> SEQ ID NO 22
<211> LENGTH: 120
<212> TYPE: DNA
<213> ORGANISM: Artificial Sequence
<220> FEATURE:
<223> OTHER INFORMATION: portion 5 in Fig. 3: a DNA fragment encoding a
      PEST sequence

<400> SEQUENCE: 22

| agccatggct | tcccgccggc | ggtggcggcg | caggatgatg | gcacgctgcc | catgtcttgt | 60 |
| gcccaggaga | gcgggatgga | ccgtcaccct | gcagcctgtg | cttctgctag | gatcaatgtg | 120 |

<210> SEQ ID NO 23
<211> LENGTH: 891
<212> TYPE: DNA
<213> ORGANISM: Artificial Sequence
<220> FEATURE:
<223> OTHER INFORMATION: portion 6 in Fig. 4: a DNA fragment encoding an
      amino acid region of the 361st to 656th amino acids in SEQ ID NO:
      2

<400> SEQUENCE: 23

| ccaaagcgaa | gagctgtctg | tgtgatgata | gtattagcat | ttataatgct | gaactatggg | 60 |
| cccatgagca | tgctggagca | agaatcccga | agagtgaaac | ctagtgtgag | ccctgccaat | 120 |
| cagaggaggc | atctcttgga | attttcagca | aaagaagtta | agacacatc | agatggtgac | 180 |
| aaccagaaag | acagttacag | ctatgatcac | tctgtgtcca | atgacaaagc | tttaatggtg | 240 |
| ctaagtgaag | agccattgct | ttatatgcct | ccacctccat | gtcaacccct | gattaacaca | 300 |
| acagagtctc | tcaggttgaa | ccatgaactt | cgaggctggg | ttcatagaca | tgaagtggaa | 360 |
| aggaccaaat | ctagaagaat | gacaaatagc | caacagaaag | cccgcattct | ccagggtgct | 420 |
| ctggaacagg | gctctaattc | tcagctgatg | gctgtccagt | acacagaaac | cactagcatc | 480 |
| agtaggaatt | ctgggagtga | gctgcaagtg | tattacgcct | cccctggaag | ttaccaaggc | 540 |
| ttctttgacg | ccatccgcag | gaggggagat | acgttttacg | ttgtctcatt | tcgaagggat | 600 |
| catctgctat | accagctac | cacccacaac | aagaccacaa | gaccaaaaat | gtcaattgta | 660 |
| ttaccagcaa | taaacataaa | tgataatgtg | atcaatgggc | aggactatga | agtaatgatg | 720 |
| cagattgact | gtcaggtgat | ggacaccagg | atcctccaca | tcaaaagctc | ctcggttccc | 780 |
| ccttatctcc | gggatcatca | gcggaaccaa | accagcacct | tctttggttc | ccctccaaca | 840 |
| accacagaga | cgacccatgt | ggtcagcacc | atccctgagt | cgttgcagta | g | 891 |

<210> SEQ ID NO 24
<211> LENGTH: 735
<212> TYPE: DNA
<213> ORGANISM: Artificial Sequence
<220> FEATURE:
<223> OTHER INFORMATION: DNA sequence inserted in an EGFPL expression
      vector

<400> SEQUENCE: 24

| ctagccacca | tggatccaaa | aaagaagaga | aaggtagatc | caaaaaagaa | gagaaaggta | 60 |
| gatccaaaaa | agaagagaaa | ggtaatggtg | agcaagggcg | aggagctgtt | caccggggtg | 120 |
| gtgcccatcc | tggtcgagct | ggacggcgac | gtaaacggcc | acaagttcag | cgtgagaggc | 180 |
| gagggcgagg | gcgatgccac | catcggcaag | ctgaccctga | agttcatctg | caccaccggc | 240 |
| aagctgcccg | tgccctggcc | cacccctcgt | gaccaccctga | cctacggcgt | gcagtgcttc | 300 |
| agccgctacc | ccgaccacat | gaagaggcac | gacttcttca | agtccgccat | gcccgaaggc | 360 |

```
tacgtccagg agcgcaccat ctctttcaag gacgacggca aatacaagac ccgcgccgta    420
gtgaagttcg agggcgacac cctggtgaac cgcatcgagc tgaagggcac tgacttcaag    480
gaggacggca acatcctggg gcacaagctg gagtacaact ttaacagcca caacgtctat    540
atcacggccg acaagcagaa gaacggcatc aaggctaact tcacagttcg ccacaacgtt    600
gaggacggca gcgtgcagct cgccgaccac taccagcaga cacccccat cggcgacggc     660 cccgtgctgc tgcccgacaa ccactacctg agcacccaga ctgtcctgag caaagacccc    720
aacgagaagt aaagc                                                     735
```

```
<210> SEQ ID NO 25
<211> LENGTH: 72
<212> TYPE: DNA
<213> ORGANISM: Artificial Sequence
<220> FEATURE:
<223> OTHER INFORMATION: portion 7 in Fig. 5: a DNA fragment encoding a
      nuclear localization signal

<400> SEQUENCE: 25
gatccaaaaa agaagagaaa ggtagatcca aaaaagaaga gaaaggtaga tccaaaaaag    60
aagagaaagg ta                                                        72

<210> SEQ ID NO 26
<211> LENGTH: 648
<212> TYPE: DNA
<213> ORGANISM: Artificial Sequence
<220> FEATURE:
<223> OTHER INFORMATION: portion 8 in Fig. 5: an amino acid region of
      the 1st to 215th amino acids in SEQ ID NO: 1

<400> SEQUENCE: 26
atggtgagca agggcgagga gctgttcacc ggggtggtgc ccatcctggt cgagctggac    60
ggcgacgtaa acggccacaa gttcagcgtg agaggcgagg gcgagggcga tgccaccatc    120
ggcaagctga ccctgaagtt catctgcacc accggcaagc tgcccgtgcc ctggcccacc    180
ctcgtgacca ccctgaccta cggcgtgcag tgcttcagcc gctaccccga ccacatgaag    240
aggcacgact tcttcaagtc cgccatgccc gaaggctacg tccaggagcg caccatctct    300
ttcaaggacg acggcaaata caagacccgc gccgtagtga agttcgaggg cgacaccctg    360
gtgaaccgca tcgagctgaa gggcactgac ttcaaggagg acggcaacat cctgggcac    420 aagctggagt acaactttaa cagccacaac gtctatatca cggccgacaa gcagaagaac    480
ggcatcaagg ctaacttcac agttcgccac aacgttgagg acggcagcgt gcagctcgcc    540
gaccactacc agcagaacac ccccatcggc gacggccccg tgctgctgcc cgacaaccac    600
tacctgagca cccagactgt cctgagcaaa gaccccaacg agaagtaa               648

<210> SEQ ID NO 27
<211> LENGTH: 197
<212> TYPE: DNA
<213> ORGANISM: Artificial Sequence
<220> FEATURE:
<223> OTHER INFORMATION: a DNA sequence used for production of an
      EGFP-ATF6d expression vector in which the spacer is changed to
      GGGS

<400> SEQUENCE: 27
tacgtaaatg ctgctgggat tacaggaggt ggcagcgact acaaagacca tgacggtgat    60
tataaagatc atgacatcga ctacaaggat gacgatgaca aggatccaaa aaagaagaga    120
```

```
aaggtagatc caaaaaagaa gagaaaggta gatccaaaaa agaagagaaa ggtactagcg      180
ctaccggact cagatct                                                    197

<210> SEQ ID NO 28
<211> LENGTH: 221
<212> TYPE: DNA
<213> ORGANISM: Artificial Sequence
<220> FEATURE:
<223> OTHER INFORMATION: a DNA sequence used for production of an
      EGFP-ATF6d expression vector in which the spacer is changed to
      GGGSGGGSGGGS

<400> SEQUENCE: 28
tacgtaaatg ctgctgggat tacaggagga ggatccggag gtggcagcgg aggtggcagc       60
gactacaaag accatgacgg tgattataaa gatcatgaca tcgactacaa ggatgacgat      120
gacaaggatc caaaaaagaa gagaaaggta gatccaaaaa agaagagaaa ggtagatcca      180
aaaaagaaga gaaaggtact agcgctaccg gactcagatc t                         221
```

The invention claimed is:

1. A polynucleotide encoding an amino acid sequence having:
    (1) a nonfluorescent peptide domain 1 of a fluorescent protein constituted of a nonfluorescent peptide domain 1 and a nonfluorescent peptide domain 2, characterized in that when nonfluorescent peptide domain 1 and nonfluorescent peptide domain 2 are associated, fluorescent activity is gained; and
    (2) an ATF6 protein domain,
    wherein the polynucleotide has a region encoding (1) at the 5' end, a region encoding (2) at the 3' end, and a region encoding a PEST sequences between the region encoding (1) and the region encoding (2),
    wherein the polynucleotide does not encode the fluorescent protein, and
    wherein the fluorescent protein is GFP, GFP mutants, or a GFP-like protein family member.

2. The polynucleotide according to claim 1, wherein the polynucleotide encodes an amino acid sequence in which the nonfluorescent peptide domain 1 of said fluorescent protein and the PEST sequences are connected via a spacer having more than 6 amino acid residues.

3. A transgenic vector comprising the polynucleotide according to claim 1.

4. A transformed cultured cell comprising a transgenic vector according to claim 3.

5. The transformed cultured cell according to claim 4, further comprising a polynucleotide encoding an amino acid sequence having:
    (3) the nonfluorescent peptide domain 2 of said fluorescent protein; and
    (4) a nuclear localization signal peptide domain,
    in a state where a protein having the amino acid sequence having (3) and (4) can be expressed.

6. The transformed cultured cell according to claim 5, wherein the transformed cultured cell is a pancreatic β-cell.

* * * * *